US005965389A

United States Patent [19]
Raymond et al.

[11] Patent Number: 5,965,389
[45] Date of Patent: *Oct. 12, 1999

[54] PRODUCTION OF GAD65 IN METHYLOTROPHIC YEAST

[75] Inventors: Christopher K. Raymond; Thomas R. Bukowski, both of Seattle; Paul D. Bishop, Fall City, all of Wash.

[73] Assignee: ZymoGenetics, Inc., Seattle, Wash.

[ * ] Notice: This patent is subject to a terminal disclaimer.

[21] Appl. No.: 08/747,108

[22] Filed: Nov. 8, 1996

Related U.S. Application Data

[63] Continuation-in-part of application No. 08/703,807, Aug. 26, 1996, and a continuation-in-part of application No. 08/703,809, Aug. 26, 1996, Pat. No. 5,716,808
[60] Provisional application No. 60/006,397, Nov. 9, 1995.
[51] Int. Cl.$^6$ .............................. C12P 21/02; C12N 1/19
[52] U.S. Cl. .................................. 435/69.1; 435/254.22; 435/254.23
[58] Field of Search ................................ 435/69.1, 254.2, 435/254.23, 320.1; 536/24.1

[56] References Cited

U.S. PATENT DOCUMENTS

| | | | |
|---|---|---|---|
| 4,808,537 | 2/1989 | Stroman et al. | 435/6 |
| 4,855,231 | 8/1989 | Stroman et al. | 435/69.1 |
| 4,879,231 | 11/1989 | Stroman et al. | 435/6 |
| 4,882,279 | 11/1989 | Cregg | 435/477 |
| 5,032,516 | 7/1991 | Cregg | 536/23.2 |
| 5,166,329 | 11/1992 | Cregg | 536/26.1 |
| 5,324,639 | 6/1994 | Brierley et al. | 435/69.4 |
| 5,389,525 | 2/1995 | Hollenberg et al. | 435/69.1 |
| 5,475,086 | 12/1995 | Tobin et al. | 530/325 |
| 5,512,447 | 4/1996 | Baekkeskov et al. | 435/7.4 |

FOREIGN PATENT DOCUMENTS

| | | |
|---|---|---|
| 0 299 108 | 1/1989 | European Pat. Off. . |
| 0 341 746 | 11/1989 | European Pat. Off. . |
| 92/05446 | 4/1992 | WIPO . |
| 92/20811 | 11/1992 | WIPO . |
| 95/04137 | 2/1995 | WIPO . |

OTHER PUBLICATIONS

Lee et al., "Taxonomic Study of ethanol–Assimilating Yeasts", *J. Gen. Appl. Microbiol.* 26:133–158 (1980).
Neumann et al., "Gene transfer into mouse lyoma cells by electroporation in high electric fields", *EMBO J.* 1:841–845 (1982).
Ledeboer et al., "Molecular cloning and characterization of a gene coding for methanol oxidase in *Hansenula polymorpha*", *Nucleic Acids Res.* 13:3063–3082 (Apr., 1985).
Ellis et al., "Isolation of Alcohol Oxidase and Two Other Methanol Regulatable Genes from the Yeast *Pichia pastoris*", *Mol. Cell. Biol.* 5:1111–1121 (May, 1985).
Cregg et al., "Functional Characterization of the Two Alcohol Oxidase Genes from the Yeast *Pichia pastoris*", *Mol. Cell. Biol.* 9:1316–1323 (Dec., 1989).
Christgau et al., "Membrane Anchoring of the Autoantigen GAD$_{65}$ to Microvesicles in Pancreatir ⊕–cells by Palmitoylation in the NH$_2$–Terminal Domain", *J. Cell. Biol.* 118: 309–320 (Jul., 1992).
Atkinson et al., "Response of peripheral–blood mononuclear cells to glutamate decarboxylase in insulin–dependent diabetes", *Lancet* 339:458–459 (1992).
Schneider et al., "Attenuated Fibrinolysis and Accelerated Atherogenesis in Type II Diabetic Patients", *Diabetes* 42:1–7 (Jan., 1993).
Tuomi et al., "Antibodies to Glutamaic Acid Decarboxylase Reveal Latent Autoimmune Diabetes Mellitus in Adults With a Non–Insulin–Dependent Onset of Disease", *Diabetes* 42:359–362 (Feb., 1993).
Mauch et al., "Baculovirus–Mediated Expression of Human 65 kDA and 67 kDa Glutamic Acid Decarboxylases in SF9 Insect Cells and Their Relevance in Diagnosis of Insulin–Dependent Diabetes Mellitus", *J. Biochem.* 113:699–704 (1993).
Hiep et al., "Transformation in the Methylotrophic Yeast *Pichia methanolica* utilizing Homologus ADE1 and Heterologous *Saccharomyces cerevisiae* ADE2 and LEU2 Genes as Genetic Markers," *Yeast* 9:1189–1197 (1993).
Shi et al., "Amino Acid Residues 24–31 but not palmitoylation of Cysteines 30 and 45 Are Required for Membrane Anchoring of Glutamic Acid Decarboxylase, GAD$_{65}$", *J. Cell Biol.* 124:927–934 (Mar., 1994).
Moody et al., Isolation by anion–exchange of immunologically and enzymatically active human islet glutamic acid decarboxylase 65 over *Diabetologia* 38:14–23 (1995).
Gellissen et al. (1992) Progress in developing methylotrophic yeasts as expression systems. TIBTech 10:413–417, Dec. 1992.

*Primary Examiner*—Nancy Degen
*Assistant Examiner*—Robert Schwartzman
*Attorney, Agent, or Firm*—Townsend and Townsend and Crew LLP

[57] ABSTRACT

Methylotrophic yeast are used for high-level expression of GAD65 that makes the production of GAD65 feasible on an industrial scale. A methanol-inducible promoter from, for example, an alcohol oxidase gene, such as *Pichia pastoris* AOX1, can be used to regulate GAD65 expression. The recombinant GAD65 has high specific activity and retains antigenic characteristics of the native molecule that are essential to immunological assays and therapeutic protocols.

56 Claims, 3 Drawing Sheets

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
       (A) LENGTH: 3077 base pairs
       (B) TYPE: nucleic acid
       (C) STRANDEDNESS: double
       (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:1:

```
CAGCTGCTCT GCTCCTTGAT TCGTAATTAA TGTTATCCTT TTACTTTGAA CTCTTGTCGG      60

TCCCCAACAG GGATTCCAAT CGGTGCTCAG CGGGATTTCC CATGAGGTTT TTGACAACTT     120

TATTGATGCT GCAAAAACTT TTTTAGCCGG GTTTAAGTAA CTGGGCAATA TTTCCAAAGG     180

CTGTGGGCGT TCCACACTCC TTGCTTTTCA TAATCTCTGT GTATTGTTTT ATTCGCATTT     240

TGATTCTCTT ATTACCAGTT ATGTAGAAAG ATCGGCAAAC AAAATATCAA CTTTTATCTT     300

GAACGCTGAC CCACGGTTTC AAATAACTAT CAGAACTCTA TAGCTATAGG GGAAGTTTAC     360

TGCTTGCTTA AAGCGGCTAA AAAGTGTTTG GCAAATTAAA AAAGCTGTGA CAAGTAGGAA     420

CTCCTGTAAA GGGCCGATTC GACTTCGAAA GAGCCTAAAA ACAGTGACTA TTGGTGACGG     480

AAAATTGCTA AAGGAGTACT AGGGCTGTAG TAATAAATAA TGGAACAGTG GTACAACAAT     540

AAAAGAATGA CGCTGTATGT CGTAGCCTGC ACGAGTAGCT CAGTGGTAGA GCAGCAGATT     600

GCAAATCTGT TGGTCACCGG TTCGATCCGG TCTCGGGCTT CCTTTTTTGC TTTTTCGATA     660

TTTGCGGGTA GGAAGCAAGG TCTAGTTTTC GTCGTTTCGG ATGGTTTACG AAAGTATCAG     720

CCATGAGTGT TTCCCTCTGG CTACCTAATA TATTTATTGA TCGGTCTCTC ATGTGAATGT     780

TTCTTTCCAA GTTCGGCTTT CAGCTCGTAA ATGTGCAAGA AATATTTGAC TCCAGCGACC     840

TTTCAGAGTC AAATTAATTT TCGCTAACAA TTTGTGTTTT TCTGGAGAAA CCTAAAGATT     900

TAACTGATAA GTCGAATCAA CATCTTTAAA TCCTTTAGTT AAGATCTCTG CAGCGGCCAG     960

TATTAACCAA TAGCATATTC ACAGGCATCA CATCGGAACA TTCAGAATGG ACTCGCAAAC    1020

TGTCGGGATT TTAGGTGGTG GCCAACTTGG TCGTATGATC GTTGAAGCTG CACACAGATT    1080

GAATATCAAA ACTGTGATTC TCGAAAATGG AGACCAGGCT CCAGCAAAGC AAATCAACGC    1140

TTTAGATGAC CATATTGACG GCTCATTCAA TGATCCAAAA GCAATTGCCG AATTGGCTGC    1200

CAAGTGTGAT GTTTTAACCG TTGAGATTGA ACATGTTGAC ACTGATGCGT TGGTTGAAGT    1260

TCAAAAGGCA ACTGGCATCA AAATCTTCCC ATCACCAGAA ACTATTTCAT TGATCAAAGA    1320

TAAATACTTG CAAAAAGAGC ATTTGATTAA GAATGGCATT GCTGTTGCCG AATCTTGTAG    1380

TGTTGAAAGT AGCGCAGCAT CTTTAGAAGA AGTTGGTGCC AAATACGGCT TCCCATACAT    1440

GCTAAAATCT AGAACAATGG CCTATGACGG AAGAGGTAAT TTTGTTGTCA AAGACAAGTC    1500

ATATATACCT GAAGCTTTGA AAGTTTTAGA TGACAGGCCG TTATACGCCG AGAAATGGGC    1560
```

-continued

| | |
|---|---|
| TCCATTTTCA AAGGAGTTAG CTGTTATGGT TGTGAGATCA ATCGATGGCC AAGTTTATTC | 1620 |
| CTACCCAACT GTTGAAACCA TCCACCAAAA CAACATCTGT CACACTGTCT TTGCTCCAGC | 1680 |
| TAGAGTTAAC GATACTGTCC AAAAGAAGGC CCAAATTTTG GCTGACAACG CTGTCAAATC | 1740 |
| TTTCCCAGGT GCTGGTATCT TTGGTGTTGA AATGTTTTTA TTACAAAATG GTGACTTATT | 1800 |
| AGTCAACGAA ATTGCCCCAA GACCTCACAA TTCTGGTCAC TATACCATCG ACGCTTGTGT | 1860 |
| CACCTCGCAA TTTGAAGCTC ATGTTAGGGC CATTACTGGT CTACCCATGC CGAAGAACTT | 1920 |
| CACTTGTTTG TCGACTCCAT CTACCCAAGC TATTATGTTG AACGTTTTAG GTGGCGATGA | 1980 |
| GCAAAACGGT GAGTTCAAGA TGTGTAAAAG AGCACTAGAA ACTCCTCATG CTTCTGTTTA | 2040 |
| CTTATACGGT AAGACTACAA GACCAGGCAG AAAAATGGGT CACATTAATA TAGTTTCTCA | 2100 |
| ATCAATGACT GACTGTGAGC GTAGATTACA TTACATAGAA GGTACGACTA ACAGCATCCC | 2160 |
| TCTCGAAGAA CAGTACACTA CAGATTCCAT TCCGGGCACT TCAAGCAAGC CATTAGTCGG | 2220 |
| TGTCATCATG GGTTCCGATT CGGACCTACC AGTCATGTCT CTAGGTTGTA ATATATTGAA | 2280 |
| GCAATTTAAC GTTCCATTTG AAGTCACTAT CGTTTCCGCT CATAGAACCC CACAAAGAAT | 2340 |
| GGCCAAGTAT GCCATTGATG CTCCAAAGAG AGGGTTGAAG TGCATCATTG CTGGTGCTGG | 2400 |
| TGGTGCCGCT CATTTACCGG GAATGGTTGC GGCGATGACG CCGCTGCCTG TTATTGGTGT | 2460 |
| CCCTGTTAAA GGCTCTACTT TGGATGGTGT TGATTCACTA CACTCCATCG TTCAAATGCC | 2520 |
| AAGAGGTATT CCTGTTGCTA CTGTGGCTAT TAACAATGCT ACTAACGCTG CCTTGCTAGC | 2580 |
| TATCACAATC TTAGGTGCCG GCGATCCAAA TACTTGTCTG CAATGGAAGT TTATATGAAC | 2640 |
| AATATGGAAA ATGAAGTTTT GGGCAAGGCT GAAAAATTGG AAAATGGTGG ATATGAAGAA | 2700 |
| TACTTGAGTA CATACAAGAA GTAGAACCTT TTATATTTGA TATAGTACTT ACTCAAAGTC | 2760 |
| TTAATTGTTC TAACTGTTAA TTTCTGCTTT GCATTTCTGA AAAGTTTAAG ACAAGAAATC | 2820 |
| TTGAAATTTC TAGTTGCTCG TAAGAGGAAA CTTGCATTCA AATAACATTA ACAATAAATG | 2880 |
| ACAATAATAT ATTATTTCAA CACTGCTATA TGGTAGTTTT ATAGGTTTGG TTAGGATTTG | 2940 |
| AGATATTGCT AGCGCTTATC ATTATCCTTA ATTGTTCATC GACGCAAATC GACGCATTTC | 3000 |
| CACAAAAATT TTCCGAACCT GTTTTTCACT TCTCCAGATC TTGGTTTAGT ATAGCTTTTG | 3060 |
| ACACCTAATA CCTGCAG | 3077 |

(2) INFORMATION FOR SEQ ID NO:2:

(i) SEQUENCE CHARACTERISTICS:
        (A) LENGTH: 3386 base pairs
        (B) TYPE: nucleic acid
        (C) STRANDEDNESS: double
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:2:

| | |
|---|---|
| GAATTCCTGC AGCCCGGGGG ATCGGGTAGT GGAATGCACG GTTATACCCA CTCCAAATAA | 60 |
| AAGTGTAGTA GCCGGACTGA AAGGTTTTAG GAGTCTGTTT GTTTGTTCAT GTGCATCATT | 120 |
| CCCTAATCTG TTAACAGTCT CGGAGTATAC AAAAAAGTAA GTCAAATATC AAGGTGGCCG | 180 |
| GGGGCAGCAT CGAGACTCGA GATGGTACAT ACTTAAAAGC TGCCATATTG AGGAACTTCA | 240 |

```
AAGTTTTATC TGTTTTTAGA ATTAAAAGAC GATTGTTGTA ACAAAACGTT GTGCCTACAT    300

AAACTCAAAT TAATGGAAAT AGCCTGTTTT GAAAAATACA CCTTCTTAAG TACTGACAAA    360

GTTTTGTTAA ATGACTATCG AACAAGCCAT GAAATAGCAC ATTTCTGCCA GTCACTTTTA    420

ACACTTTCCT GCTTGCTGGT TGACTCTCCT CATACAAACA CCCAAAAGGG AAACTTTCAG    480

TGTGGGGACA CTTGACATCT CACATGCACC CCAGATTAAT TTCCCCAGAC GATGCGGAGA    540

CAAGACAAAA CAACCCTTTG TCCTGCTCTT TTCTTTCTCA CACCGCGTGG GTGTGTGCGC    600

AGGCAGGCAG GCAGGCAGCG GGCTGCCTGC CATCTCTAAT CGCTGCTCCT CCCCCCTGGC    660

TTCAAATAAC AGCCTGCTGC TATCTGTGAC CAGATTGGGA CACCCCCCTC CCCTCCGAAT    720

GATCCATCAC CTTTTGTCGT ACTCCGACAA TGATCCTTCC CTGTCATCTT CTGGCAATCA    780

GCTCCTTCAA TAATTAAATC AAATAAGCAT AAATAGTAAA ATCGCATACA AACGTCATGA    840

AAAGTTTTAT CTCTATGGCC AACGGATAGT CTATCTGCTT AATTCCATCC ACTTTGGGAA    900

CCGCTCTCTC TTTACCCCAG ATTCTCAAAG CTAATATCTG CCCCTTGTCT ATTGTCCTTT    960

CTCCGTGTAC AAGCGGAGCT TTTGCCTCCC ATCCTCTTGC TTTGTTTCGG TTATTTTTTT   1020

TTCTTTTGAA ACTCTTGGTC AAATCAAATC AAACAAAACC AAACCTTCTA TTCCATCAGA   1080

TCAACCTTGT TCAACATTCT ATAAATCGAT ATAAATATAA CCTTATCCCT CCCTTGTTTT   1140

TTACCAATTA ATCAATCTTC AAATTTCAAA TATTTTCTAC TTGCTTTATT ACTCAGTATT   1200

AACATTTGTT TAAACCAACT ATAACTTTTA ACTGGCTTTA GAAGTTTTAT TTAACATCAG   1260

TTTCAATTTA CATCTTTATT TATTAACGAA ATCTTTACGA ATTAACTCAA TCAAAACTTT   1320

TACGAAAAAA AAATCTTACT ATTAATTTCT CAAAATGGCT ATTCCAGATG AATTTGATAT   1380

TATTGTTGTC GGTGGTGGTT CCACCGGTTG TGCTCTTGCT GGTAGATTAG GTAACTTGGA   1440

CGAAAACGTC ACAGTTGCTT TAATCGAAGG TGGTGAAAAC AACATCAACA ACCCATGGGT   1500

TTACTTACCA GGTGTTTATC CAAGAAACAT GAGATTAGAC TCAAAGACTG CTACTTTTTA   1560

CTCTTCAAGA CCATCACCAC ACTTGAACGG TAGAAGAGCT ATTGTTCCAT GTGCTAACAT   1620

CTTGGGTGGT GGTTCTTCCA TCAACTTCTT GATGTACACC AGAGCCTCTG CCTCCGATTA   1680

CGATGATTGG GAATCTGAAG GTTGGACTAC CGATGAATTA TTACCACTAA TGAAGAAGAT   1740

TGAAACTTAT CAAAGACCAT GTAACAACAG AGAATTGCAC GGTTTCGATG GTCCAATTAA   1800

GGTTTCATTT GGTAACTATA CTTATCCAAA CGGTCAAGAT TTCATTAGAG CTGCCGAATC   1860

TCAAGGTATT CCATTTGTTG ATGATGCTGA AGATTTGAAA TGTTCCCACG GTGCTGAGCA   1920

CTGGTTGAAG TGGATCAACA GAGACTTAGG TAGAAGATCC GATTCTGCTC ATGCTTACAT   1980

TCACCCAACC ATGAGAAACA AGCAAAACTT GTTCTTGATT ACTTCCACCA AGTGTGAAAA   2040

GATTATCATT GAAAACGGTG TTGCTACTGG TGTTAAGACT GTTCCAATGA AGCCAACTGG   2100

TTCTCCAAAG ACCCAAGTTG CTAGAACTTT CAAGGCTAGA AAGCAAATTA TTGTTTCTTG   2160

TGGTACTATC TCATCACCAT TAGTTTTGCA AGATCTGGT ATCGGTTCCG CTCACAAGTT   2220

GAGACAAGTT GGTATTAAAC CAATTGTTGA CTTACCAGGT GTTGGTATGA ACTTCCAAGA   2280

TCACTACTGT TTCTTCACTC CATACCATGT CAAGCCAGAT ACTCCATCAT TCGATGACTT   2340

TGTTAGAGGT GATAAAGCTG TTCAAAAATC TGCTTTCGAC CAATGGTATG CTAACAAGGA   2400

TGGTCCATTA ACCACTAATG GTATTGAGGC AGGTGTTAAG ATTAGACCAA CTGAAGAAGA   2460

ATTAGCCACT GCTGATGACG AATTCAGAGC TGCTTATGAT GACTACTTTG GTAACAAGCC   2520

AGATAAGCCA TTAATGCACT ACTCTCTAAT TTCTGGTTTC TTTGGTGACC ACACCAAGAT   2580

TCCAAACGGT AAGTACATGT GCATGTTCCA CTTCTTGGAA TATCCATTCT CCAGAGGTTT   2640
```

```
CGTTCACGTT GTTTCTCCAA ACCCATACGA TGCTCCTGAC TTTGATCCAG GTTTCATGAA    2700

CGATCCAAGA GATATGTGGC CAATGGTTTG GTCTTACAAG AAGTCCAGAG AAACTGCCAG    2760

AAGAATGGAC TGTTTTGCCG GTGAAGTTAC TTCTCACCAC CCACACTACC CATACGACTC    2820

ACCAGCCAGA GCTGCTGACA TGGACTTGGA AACTACTAAA GCTTATGCTG GTCCAGACCA    2880

CTTTACTGCT AACTTGTACC ACGGTTCATG GACTGTTCCA ATTGAAAAGC CAACTCCAAA    2940

GAACGCTGCT CACGTTACTT CTAACCAAGT TGAAAAACAT CGTGACATCG AATACACCAA    3000

GGAGGATGAT GCTGCTATCG AAGATTACAT CAGAGAACAC ACTGAAACCA CATGGCATTG    3060

TCTTGGTACT TGTTCAATGG CTCCAAGAGA AGGTTCTAAG GTTGTCCCAA CTGGTGGTGT    3120

TGTTGACTCC AGATTAAACG TTTACGGTGT TGAAAAGTTG AAGGTTGCTG ATTTATCAAT    3180

TTGCCCAGAT AATGTTGGTT GTAACACTTA CTCTACTGCT TTGTTAATCG GTGAAAAGGC    3240

TTCTACCTTA GTTGCTGAAG ACTTGGGCTA CTCTGGTGAT GCTTTGAAGA TGACTGTTCC    3300

AAACTTCAAA TTGGGTACTT ATGAAGAAGC TGGTCTAGCT AGATTCTAGG GCTGCCTGTT    3360

TGGATATTTT TATAATTTTT GAGAGT                                        3386

(2) INFORMATION FOR SEQ ID NO:3:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:3:

TGATCACCTA GGACTAGTGA CAAGTAGGAA CTCCTGTA                              38

(2) INFORMATION FOR SEQ ID NO:4:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:4:

CAGCTGCCTA GGACTAGTTT CCTCTTACGA GCAACTAGA                             39

(2) INFORMATION FOR SEQ ID NO:5:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:5:

TGGTTGAAGT GGATCAA                                                     17

(2) INFORMATION FOR SEQ ID NO:6:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:6:

GTGTGGTCAC CGAAGAA                                                     17
```

(2) INFORMATION FOR SEQ ID NO:7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (vii) IMMEDIATE SOURCE:
        (B) CLONE: ZC9885

(xi) SEQUENCE DESCRIPTION: SEQ ID NO:7:

```
GTTGTTCCTT CCAAACCATT GAAC                                          24
```

(2) INFORMATION FOR SEQ ID NO:8:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (vii) IMMEDIATE SOURCE:
        (B) CLONE: ZC9883

(xi) SEQUENCE DESCRIPTION: SEQ ID NO:8:

```
AAAGTAAGAA GCGTAGCCTA GTTG                                          24
```

(2) INFORMATION FOR SEQ ID NO:9:

(i) SEQUENCE CHARACTERISTICS:
        (A) LENGTH: 329 base pairs
        (B) TYPE: nucleic acid
        (C) STRANDEDNESS: double
        (D) TOPOLOGY: linear (xi) SEQUENCE DESCRIPTION: SEQ ID NO:9:

```
GACCATGATT ACGCCAAGCG CGCAATTAAC CCTCACTAAA GGGAACAAAA GCTGGGTACC     60

GGGCCCCCCC TCGAGGTCGA CGGTATCGAT AAGCTTTATT ATAACATTAA TATACTATTT    120

TATAACAGGA TTGAAAATTA TATTTATCTA TCTAAAACTA AAATTCAAAA TGGCTATTCC    180

TGAAGAATTC GATATCATTG TTGTCGGTGG TGGTTCTGCC GGCTGTCCTA CTGCTGGTAG    240

ATTGGCTAAC TTAGACCCAA ATTTAACTGT TGCTTTAATC GAAGCTGGTG AAAACAACAT    300

TAACAACCCA TGGGTCTACT TACCAGGCG                                     329
```

PRODUCTION OF GAD65 IN METHYLOTROPHIC YEAST

RELATED APPLICATIONS

The present invention is a continuation-in-part of U.S. Ser. No. 08/703,807, filed Aug. 26, 1996 and U.S. Ser. No. 08/703,809, filed Aug. 26, 1996, U.S. Pat. No. 5,716,808, and claims benefit of U.S. Provisional Application 60/006, 397, filed November 9, 1995, each of which is expressly incorporated herein in its entirety by reference.

BACKGROUND OF THE INVENTION

L-Glutamic acid decarboxylase (GAD) catalyzes the synthesis of γ-aminobutyric acid (GABA), which is widely accepted as the major inhibitory neurotransmitter in the mammalian brain. One isoform of GAD has been identified as a 65 kD beta cell autoantigen in the pancreatic islets of Langerhans. Type 1 (insulin-dependent) Diabetes mellitus (IDDM) is an autoimmune disease that leads to the destruction of the pancreatic beta-cells. Development of IDDM has been associated with the presence of autoantibodies to the 65 kD GAD enzyme.

Naturally occurring GAD65 is difficult to isolate from pancreatic islet cells in meaningful quantity and purity, and purified GAD has been isolated from COS cells in only trace amounts. Tuomi et al., *Diabetes* 42:359–362 (1993). The cloning of human islet cell $GAD_{65}$ makes it theoretically possible to obtain recombinant protein useful as antigen in quantitative assays for measuring GAD autoantibodies in IDDM susceptible individuals. GAD65 has been expressed in bacterial (e.g., Atkinson et al., *Lancet* 339:458–459 (1992)), mammalian (e.g., Hagopian et al., *Diabetes* 42:1–3 (1993)), and insect cells (e.g., Christgau et al., *J. Cell. Biol.* 118:309–320 (1992)). These strategies provided partially purified material for the detection of autoantibodies on a small scale. However, they were not fully successful as sources of purified GAD, either because the level of expression was low, making purification difficult, enzymatic activity was reduced, or because the GAD65 was expressed as a fusion protein which might have altered the immunoreactivity of the GAD65 portion of the molecule. For example, the amount of GAD65 expressed from BHK cells was approximately 600 μg/liter (Moody et al., *Diabetologia* 38:14–23 (1995), which made purification by affinity chromatography essential.

GAD65 is a complex molecule, containing 15 cysteine residues and two palmitoylated sites (Shi et al., *J. Cell Biol.* 124:927–934 (1994)). In solution GAD65 aggregates rapidly to form both covalent and non-covalently bound oligomers having reduced enzymatic activity and reduced ability to react with antibodies. These characteristics make the purification of recombinant GAD65 difficult. The material is often purified at high concentration under which conditions its inherent tendency to irreversibly aggregate leads to the formation of unusable precipitates.

The production of large quantities of GAD65 is sought as a source of antigen for development of immunoassays and potentially for use in screening and monitoring large numbers of individuals for susceptibility to Type 1 diabetes. However, large quantities of recombinant GAD65 are of little use if the biological characteristics of the molecule, such as antigenic properties and enzymatic activity, are impaired.

More recently GAD65 has been expressed in insect cells, such as *Spodoptera frugiperda* (Sf9) cells, using baculovirus vectors. Moody et al., supra; Mauch et al., *J. Biochem.* 113:699–704 (1993); and Christgau et al., *J. Cell. Biol.* 118:309–320 (1992). The recombinant GAD65 was reportedly obtained in large quantities from the insect cells (up to 50 mg/L) and could be purified up to 95% purity while retaining significant enzymatic and antigenic reactivity. Moody et al., ibid. However, insect cell expression systems suffer from a number of disadvantages when used for protein expression on an industrial scale. For example, the insect cells are difficult to manipulate in quantities needed to cells (1) are expensive to culture; (2) require infection with baculovirus for heterologous protein expression, making them unsuitable for continuous production methods; (3) produce poorly reproducible results, making them difficult to rigorously validate; and (4) have a low overall productivity rate.

What is needed in the art is a means for convenient expression of very large amounts of biologically active recombinant GAD65. The protein preparations isolated from the expression system should be readily purified to relative homogeneity, while retaining a high level of enzymatic and antigenic activity. Quite surprisingly, the present invention fulfills these and other related needs.

SUMMARY OF THE INVENTION

In one embodiment the present invention provides an essentially pure culture of a methylotrophic yeast for expression of GAD65. The yeast is capable of growth on methanol as a carbon and energy source, and is transformed with a DNA construct comprising the operatively linked elements of a methanol-inducible transcriptional promoter, a DNA segment encoding a GAD65 polypeptide, a transcriptional terminator; and a selectable marker. The methylotrophic yeast is selected from Pichia, Hansenula, Torulopsis or Candida, and preferably is *Pichia pastoris* or *Pichia methanolica*. The methanol-inducible promoter and the transcriptional terminator of the transforming DNA construct can be from an alcohol oxidase gene, such as the *P. pastoris* AOX1 gene. Preferably the GAD65 polypeptide is human GAD65.

In another embodiment the invention provides a DNA construct for expressing GAD65 in methylotrophic yeast. The construct comprises the operatively linked elements of a methanol-inducible transcriptional promoter, such as from an alcohol oxidase gene, e.g., *P. pastoris* AOX1; a DNA segment encoding a GAD65 islet cell polypeptide, preferably a human GAD65 polypeptide; a transcriptional terminator, such as from an alcohol oxidase gene, e.g., *P. pastoris* AOX1; and a selectable marker.

In yet another embodiment the present invention provides a method for purifying GAD65 expressed by a culture of methylotrophic yeast cells. The method comprises the steps of isolating a GAD65-containing cell fraction from the yeast cell culture (e.g., by lysing the yeast cells) in a buffer containing a reducing agent and a detergent; phase-partitioning the GAD65-containing cell fraction into a GAD65-containing detergent phase and an aqueous phase; separating the GAD65 from the GAD65-containing detergent phase by anion exchange chromatography in a buffer containing a reducing agent and a detergent to produce a GAD65 anion exchange fraction; applying the first GAD65 anion exchange fraction to a column containing a cation exchange medium at a slightly acidic pH and adjusting the GAD65-containing fraction therefrom to an alkaline pH; loading the GAD65 cation exchange fraction on a second anion exchange column at an alkaline pH in a buffer containing a reducing agent (e.g., dithiothreitol or 2-mercaptoethanol) and a detergent (e.g., a non-ionic detergent, such as Triton X-114, Triton X-100, or n-octylglucoside), eluting the GAD65 in an alkaline to acid pH gradient (e.g., between about pH 8 and about pH 4), and adjusting the pH of the GAD65 eluate to about neutral; and purifying the GAD65 anion exchange eluate by hydroxyapatite chromatography in a buffer containing a reducing agent and a detergent, and obtaining purified GAD65. The GAD65 is preferably eluted from the hydroxyapatite with a gradient of potassium phosphate. In a related aspect, prior to separating the GAD65 from the GAD65-containing detergent phase by anion exchange chromatography, the method further comprises the step of removing yeast cell particulate from the GAD65-containing detergent phase. Moreover, prior to the step of purifying, the GAD65 second anion exchange eluate can be fractionated further on a quaternary ammonium exchange column. In an alternative method, a first anion exchange chromatography step of the GAD65-containing yeast cell fraction is employed prior to phase partitioning, and a cationic exchange step is omitted.

In another aspect the invention provides a method of preparing an essentially pure culture of a methylotrophic yeast strain that produces a GAD65 polypeptide. A methylotrophic yeast host is transformed with a DNA construct having, as operatively linked elements, a methanol-inducible transcriptional promoter, a DNA segment encoding the GAD65 polypeptide, a transcriptional terminator, and a selectable marker. The transformed cells are then cultured under conditions wherein the DNA segment is expressed and the GAD65 polypeptide is produced. The level of GAD65 polypeptide produced by isolates of the transformed cells is assayed and isolates that produce high levels of GAD65 polypeptide are selectively cultured.

DESCRIPTION OF THE SPECIFIC EMBODIMENTS

Figure 1:
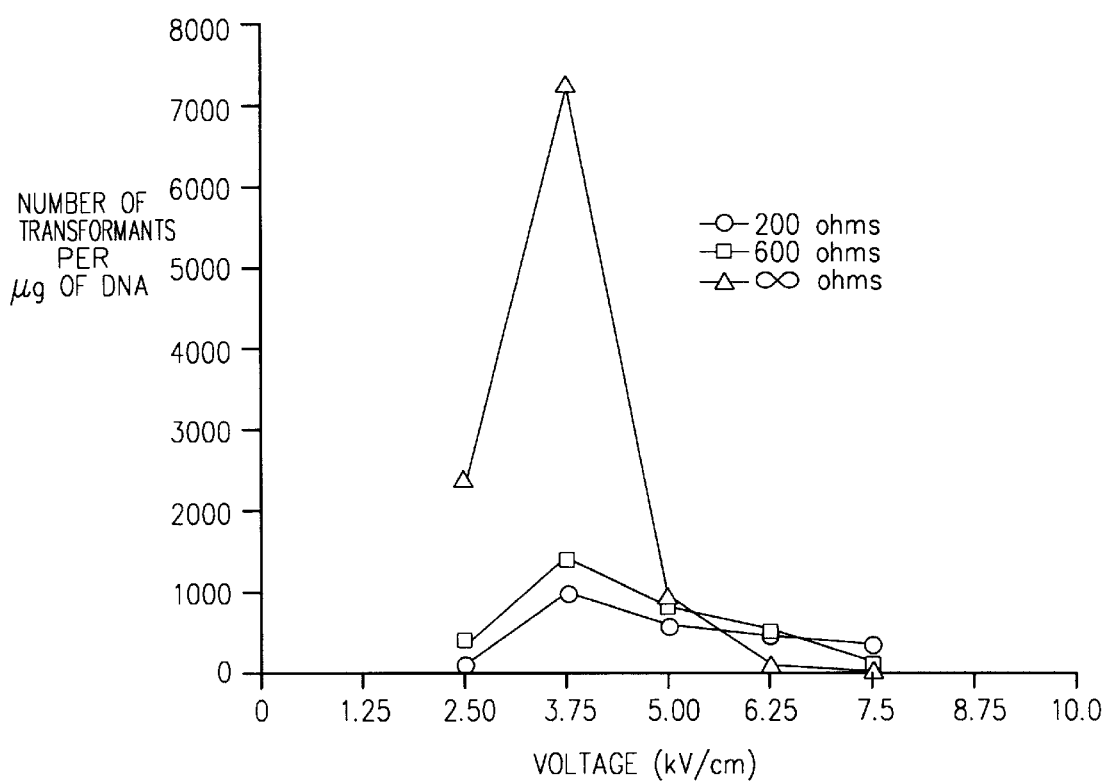
FIG. 1 illustrates the effects of field strength and pulse duration on electroporation efficiency of *P. methanolica*.

The present invention provides recombinant GAD65 produced in methylotrophic yeast, i.e., yeast which are able to utilize methanol as a sole source of carbon and energy. Species of yeasts which have the biochemical pathways necessary for methanol utilization fall into four genera, Hansenula, Pichia, Candida, and Torulopsis. Within these genera species of Pichia are preferred, e.g., *Pichia pastoris* and *Pichia methanolica*, as is *Hansenula polymorpha*. For commercial scale protein production it is particularly preferred to use a strain that can efficiently utilize a second carbon source (e.g., glycerol) in addition to methanol. Also provided are methods for isolating GAD65 produced by the methylotrophic yeast and purifying the GAD65 to substantial purity in a form that is biologically and enzymatically active.

The methylotrophic yeast grow rapidly to high biomass on minimal defined media, and gene expression can be driven by a strong, tightly regulated promoter. There are a number of methanol responsive genes in methylotrophic yeast, the expression of each being controlled by methanol responsive promoters, which promoters can be used to control the expression of GAD65. Most commonly, expression of a GAD65 in methylotrophic yeast is driven by a promoter of an alcohol oxidase structural gene, such as the AOX1 gene of *P. pastoris*, the AOX2 gene of *P. pastoris* (U.S. Pat. Nos. 4,855,231, 5,032,516 and 5,166,329, incorporated herein by reference), the MOX1 gene of *Hansenula polymorpha* or *Candida biodinii* (U.S. Pat. No. 5,389,525, incorporated herein by reference), the methanol utilization genes AUG1 and AUG2 of *P. methanolica*, or the like. The expression level of the AOX1 mRNA is tightly regulated with respect to carbon source, and the AOX1 promoter is a strong, tightly regulated promoter for the expression of GAD65. The sequences of alcohol oxidase genes of other methylotrophic yeast are known, e.g., Cregg et al., *Mol. Cell. Biol.* 9:1316–1323 (1989); Ellis et al., *Mol. Cell. Biol.* 5:1111–1121 (1985); and Ledeboer et al., *Nucleic Acids Res.* 13:3063–3082 (1985), each of which is incorporated herein by reference, and these genes share distinct regions of identity. Other methylotrophic yeasts include, for example, *Pichia cellobiosa, Candida boidinii, Candida cariosilignicola, Candida succiphila, Torulopsis molischiana*, and *Hansenula capsulata* (Lee and Komagata, *J. Gen. Appl. Microbiol.* 26:133–158 (1980)). To clone the promoter/terminator portions of the alcohol oxidase gene of other species or strains, PCR primers are used to amplify genomic segments from the desired species or strain of methylotrophic yeast based on the described sequences of AOX1, AOX2, or other related gene. The PCR amplified fragments are sequenced and clones that encode alcohol oxidase coding sequences are identified. These are used as hybridization probes to identify full length genomic clones of the alcohol oxidase gene from a genomic clone bank of the species or strain of interest. The entire alcohol oxidase gene is sequenced and promoter/terminator regions identified. By analogy to the *P. pastoris* AOX1 regulatory region, the promoter, mRNA start site, and 5' untranslated region of the alcohol oxidase gene occupy a regions within about 1 kb upstream of the alcohol oxidase ATG start codon, and the alcohol oxidase transcriptional termination regions is found within about 500 bp of the alcohol oxidase stop codon. Site directed mutagenesis or the like is used to eliminate the alcohol oxidase coding region and to generate useful cloning sites for inserting cDNA encoding GAD65 between the promoter/terminator regions.

As an alternative to the alcohol oxidase promoter/terminator, the promoter of another methanol responsive structural gene product can be cloned and employed to drive the expression of GAD65. These genes include those which encode other enzymes important in the methanol utilization pathway, such as dihydroxyacetone synthase (DAS), formate dehydrogenase (FMD), formaldehyde dehydrogenase, catalase, etc. See, Veenhuis et al., *Adv. Microbial Physiol.* 24:1–82 (1983); U.S. Pat. No. 5,389,525; Janowicz et al., Nuc. Acids Res. 13: 3043–3062 (1985); Tschopp et al., *Nuc. Acids Res.* 15:3859–3876 (1987); Hollenberg and Janowicz, EPO publication 0 299 108; Didion and Roggenkamp, *FEBS Lett.* 303:113, (1992). Other methanol responsive genes can be cloned on the basis of activity or sequence (e.g., by PCR or hybridization). To identify and clone methanol responsive genes it is advantageous to utilize a differential cDNA library to identify genes expressed in cells grown on methanol but not in cells grown on an alternative carbon source (e.g., glucose). The methanol induced gene thereby serves as a source for a methanol regulated promoter and transcriptional terminator. The identification and cloning of methanol inducible genes obtained from Pichia is also described in Stroman et al., U.S. Pat. No. 4,808,537, incorporated herein by reference.

For expression of GAD65 in a methylotrophic yeast, a polynucleotide sequence (e.g., cDNA) encoding GAD65 or a desired polypeptide fragment of GAD65 is inserted into a suitable expression vector, which in turn is used to transform a selected methylotrophic yeast, preferably P. pastoris or P. methanolica, for expression. Expression vectors for use in carrying out the present invention comprise a methanol responsive promoter, such as the AOXI promoter, or other methanol inducible promoter operatively linked to and capable of directing the transcription of the cloned GAD65 DNA, and a transcriptional terminator operatively linked to the GAD65 DNA. (The term "operatively linked" indicates that the segments are arranged so that they function in concert for their intended purposes, e.g., transcription initiates in the promoter and proceeds through the coding segment to the terminator; see Sambrook et al., infra.) For expression of GAD65 in methylotrophic yeast, it is preferred that the promoter and terminator be from host species genes. The expression vectors may contain additional elements, such as an origin of replication, one or more selectable markers allowing amplification in alternative hosts, unique restriction sites into which a GAD65 encoding gene is inserted such as, e.g., EcoRI, etc. Expression vectors suitable for insertion and expression of the GAD65 polynucleotide sequences are also available from commercial suppliers, such as a Pichia Expression Kit supplied by Invitrogen, San Diego, Calif.

A particularly preferred methanol-inducible promoter is that of a P. methanolica alcohol utilization gene. A representative coding strand sequence of one such gene, AUG1, is shown in SEQ ID NO:2. Within SEQ ID NO:2, the initiation ATG codon is at nucleotides 1355–1357. Nucleotides 1–23 of SEQ ID NO:2 are non-AUG1 polylinker sequence. It is particularly preferred to utilize as a promoter a segment comprising nucleotides 24–1354 of SEQ ID NO:2, although additional upstream sequence can be included. P. methanolica contains a second alcohol utilization gene, AUG2, the promoter of which can be used within the present invention. A partial DNA sequence of one AUG2 clone is shown in SEQ ID NO:9. AUG2 promoter segments used within the present invention will generally comprise nucleotides 91–169 of SEQ ID NO:9, although small truncations at the 3' end would not be expected to negate promoter function.

Vectors for expression of GAD65 in methylotrophic yeast will include a selectable marker for selection and maintenance in the yeast host. The marker will in general be one that provides for biosynthesis of amino acids or nucleotides. Exemplary selectable marker genes include, but are not limited to, the ARG4 (argininosuccinate lyase) genes from P. pastoris and S. cerevisiae, the HIS4 (histidinol dehydrogenase) genes from P. pastoris and S. cerevisiae, the uracil utilization gene (URA), genes providing the capacity for leucine or adenine synthesis, and the like.

A preferred selectable marker for use in Pichia methanolica is a P. methanolica ADE2 gene, which encodes phosphoribosyl-5-aminoimidazole carboxylase (AIRC; EC 4.1.1.21), and is also described in copending applications U.S. Ser. Nos. 08/703,807 and 08/703,809, the entire disclosures of which are incorporated herein by reference. The ADE2 gene, when transformed into an ade2 host cell, allows the cell to grow in the absence of adenine. The coding strand of a representative P. methanolica ADE2 gene sequence is shown in SEQ ID NO:1. The sequence illustrated includes 1006 nucleotides of 5' non-coding sequence and 442 nucleotides of 3' non-coding sequence, with the initiation ATG codon at nucleotides 1007–1009. Within a preferred embodiment of the invention, a DNA segment comprising nucleotides 407–2851 is used as a selectable marker, although longer or shorter segments could be used as long as the coding portion is operably linked to promoter and terminator sequences. Those skilled in the art will recognize that this and other sequences provided herein represent single alleles of the respective genes, and that allelic variation is expected to exist. Any functional ADE2 allele can be used within the present invention. Other nutritional markers that can be used within the present invention include the P. methanolica ADE1, HIS3, and LEU2 genes, which allow for selection in the absence of adenine, histidine, and leucine, respectively. Heterologous genes, such as genes from other fungi, can also be used as selectable markers. For large-scale, industrial processes where it is desirable to minimize the use of methanol, it is preferred to use host cells in which both methanol utilization genes (AUG1 and AUG2) are deleted.

The DNA constructs may further contain additional elements, such as an origin of replication and a selectable marker that allow amplification and maintenance of the DNA in an alternate host (e.g., E. coli). To facilitate integration of the DNA into the host chromosome, it is preferred to have the entire expression segment, comprising the promoter—gene of interest—terminator plus selectable marker, flanked at both ends by host DNA sequences. This is conveniently accomplished by including 3' untranslated DNA sequence at the downstream end of the expression segment and relying on the promoter sequence at the 5' end. When using linear DNA, the expression segment will be flanked by cleavage sites to allow for linearization of the molecule and separation of the expression segment from other sequences (e.g., a bacterial origin of replication and selectable marker). Preferred cleavage sites are those that are recognized by restriction endonucleases that cut infrequently within a DNA sequence, such as those that recognize 8-base target sequences (e.g., Not I).

cDNA sequences encoding GAD65 and homologous proteins thereof are described in, e.g., PCT publication WO 92/20811, incorporated herein by reference. By "GAD65" is meant recombinant islet cell GAD65 polypeptides, i.e., a polypeptide produced by a recombinant expression system and typically free of native endogenous substances. By "polypeptide" is meant to include sequences of at least about 10 to 25 amino acids, up to 100–200 amino acids or more, including up to the entire islet GAD protein, as shown in, e.g., FIG. 2 of the PCT WO92/20811 publication. When the polypeptide comprises the entire GAD protein, the polypeptides will be substantially homologous to the entire islet cell GAD sequence as disclosed in FIG. 2 of PCT publication WO 92/20811. Preferably the GAD65 sequence is of human origin, but GAD65 sequences of other species can also be used. By substantially homologous polypeptides is meant to include those sequences which have at least about 85% homology, preferably at least 90%, and more preferably at least about 95% or more homology to the amino acid sequence of the human islet cell GAD sequence(s) and still retain at least some biological activity of the native GAD. By biological activity is meant the ability to catalyze the decarboxylation of L-glutamic acid, to specifically bind antibodies which bind to the native human islet cell GAD protein (i.e., autoantibodies to human islet cell GAD), and/or to elicit antibodies which also bind to the native protein. When the polypeptide of the invention comprises less than the entire GAD protein, the polypeptide will preferably be substantially homologous to a portion of at least about 10, more usually at least about 15 amino acids of a desired region of the GAD65 protein. For example, certain sequence domains are variable, differing at least about 15%, more typically at least about 20%, from analogous regions of GADs of other tissues and/or species, while other regions of the islet cell GAD are identical or nearly identical to other GADs, and thus represent conserved regions. The conserved and variable sequence regions of the human islet cell GAD and homology thereof can be determined by techniques known to the skilled artisan, such as sequence alignment techniques.

As will be appreciated by those skilled in the art, the GAD65 which is expressed as part of the present invention also includes those GAD65 polypeptides having slight variations in amino acid sequences or other properties. Such variations may arise naturally as allelic variations (e.g., due to genetic polymorphism) or may be produced by human intervention (e.g., by mutagenesis of cloned DNA sequences), such as induced point, deletion, insertion and substitution mutants. Minor changes in amino acid sequence are generally preferred, such as conservative amino acid replacements, small internal deletions or insertions, and additions or deletions at the ends of the molecules. Substitutions may be designed based on, for example, the model of Dayhoff, et. al. (in *Atlas of Protein Sequence and Structure* 1978, Nat'l Biomed. Res. Found., Washington, D.C.). These modifications can result in changes in the amino acid sequence, provide silent mutations, modify a restriction site, or provide other specific mutations. The polypeptides may comprise one or more selected antigenic determinants of GAD65, possess catalytic activity exhibited by native GAD65 protein or alternatively lack such activity, mimic GAD65 binding regions, or the like.

In the context of the present invention, the expression vector or DNA construct for expressing GAD65 in methylotrophic yeast comprises segments which are operatively linked with one another so as to express a functional GAD65 polypeptide in methylotrophic yeast. The DNA construct comprises a methanol regulated methylotrophic yeast promoter segment, a segment encoding GAD65, and a transcriptional terminator. Thus, the GAD65 encoding segment is transcribed under regulation of the promoter region into a transcript capable of providing, upon translation, the desired GAD65 polypeptide. The DNA construct may also include sequences allowing for its replication in bacteria and selectable markers, as described herein. The GAD65 may be secreted or intracellular, and preferably is intracellular. For secretion, a signal sequence may be supplied, e.g., the *S. cerevisiae* prepro alpha mating factor (MFα prepro) leader sequence, as described in, e.g., U.S. Pat. No. 5,324,639 and Vedvick et al., *J. Ind. Microbiol.* 7:197–201 (1991), incorporated herein by reference.

The DNA constructs containing DNA sequences encoding GAD65 may be introduced into essentially pure cultures of methylotrophic yeast cells by, for example, transforming spheroplasts that have been produced by enzymatic digestion of the cell walls. The transforming DNA is incubated in the presence of calcium ions and polyethylene glycol, then the cells walls are regenerated in selective growth medium. See, e.g., Stroman et al., U.S. Pat. No. 4,879,231, incorporated herein by reference. Transformation of whole cells of methylotrophic species of the genus Pichia in buffered solutions of lithium chloride or lithium sulfate are described in Cregg et al., U.S. Pat. No. 4,949,555, incorporated herein by reference. Other techniques for introducing cloned DNA sequences into yeast cells, such as electroporation (Neumann et al., *EMBO J.* 1:841–845, 1982), may also be used. By this latter method, for example, cells are grown in rich media, then washed twice with water and once with 1.2 M sorbitol. The cells are then concentrated ~100-fold in 1.2 M sorbitol. DNA is added to these "competent" cells, which are then pulsed in a standard 2 mm electroporation cuvette at 1.5 V, 25 $\mu$F, and 200 $\Omega$. For transformation of *P. methanolica*, it has been found that electroporation is surprisingly efficient when the cells are exposed to an exponentially decaying, pulsed electric field having a field strength of from 2.5 to 4.5 kV/cm and a time constant ($\tau$) of from 1 to 40 milliseconds. The time constant $\tau$ is defined as the time required for the initial peak voltage $V_0$ to drop to a value of $V_0/e$. The time constant can be calculated as the product of the total resistance and capacitance of the pulse circuit, i.e., $\tau = R \times C$. Typically, resistance and capacitance are either preset or may be selected by the user, depending on the electroporation equipment selected. An electroporation protocol is described in U.S. Ser. No. 08/683,500, incorporated herein by reference.

Pulsed cells are plated on standard selective media, such as minimal plates lacking histidine when using a HIS4 selectable marker. The primary alcohol oxidase gene of the host cells may be disrupted using site-directed mutagenesis or the like, as described in Cregg, U.S. Pat. No. 4,882,279, incorporated herein by reference. Positive transformants are characterized by Southern blot analysis (Sambrook et al., *Molecular Cloning, A Laboratory Manual*, Cold Spring Harbor Laboratory Press, Cold Spring Harbor, NY (1989), incorporated herein by reference) for the site of DNA integration, Northern blot analysis for methanol-responsive GAD65 gene expression, and Western blot or the like for the presence of GAD65 in disrupted cells or in the culture medium when the GAD65 is secreted. It is preferred to use Western blotting to screen for high producing transformants. A stability test is then performed, typically by assaying 1,000 colonies for uniform expression levels. High yielding, stable transformants are then chosen for further development.

To maximize the stability of GAD65 expression in methylotrophic yeast, GAD65 expression vectors are integrated into the host cell genome to produce integrative transformants. For example, cleavage of a vector within a sequence shared by the host genome, e.g., AOX1, HIS4, etc. stimulates homologous recombination events that target integration of the vector to that genomic locus. Methods have also been described for constructing *P. pastoris* strains with multiple integrated copies of a heterologous gene cassette, e.g., U.S. Pat. No. 4,895,800, incorporated herein by reference. Multi-copy expression strains can also be identified by screening a transformed cell population by colony dot-blot hybridization for transformants with multiple copies of the GAD65-encoding gene (e.g., Romanos et al., *Vaccine* 9:901–906 (1991), incorporated herein by reference), or by introducing multiple expression cassette copies into a single vector prior to transformation. Integrative transformants are preferred for use in protein production processes. Such cells can be propagated without continuous selective pressure because DNA is rarely lost from the genome. Integration of DNA into the host chromosome can be confirmed by Southern blot analysis. Briefly, transformed and untransformed host DNA is digested with restriction endonucleases, separated by electrophoresis, blotted to a support membrane, and probed with appropriate host DNA segments. Differences in the patterns of fragments seen in untransformed and transformed cells are indicative of integrative transformation. Restriction enzymes and probes can be selected to identify transforming DNA segments (e.g., promoter, terminator, heterologous DNA, and selectable marker sequences) from among the genomic fragments.

Host cells containing DNA constructs of the present invention are then cultured to produce recombinant GAD65. The cells are cultured according to accepted methods in a culture medium containing nutrients required for growth of methylotrophic yeast, e.g., a minimal defined medium with an excess of non-inducing carbon source (e.g., glycerol). The growth medium will generally select for cells containing the DNA construct by, for example, drug selection or deficiency in an essential nutrient which is complemented by the selectable marker on the DNA construct. Expression of GAD65 is induced by limiting the non-inducing carbon source and, preferably, by adding the inducing carbon source, e.g., methanol, so as to derepress the methanol responsive promoter. Transformed cells which are particularly well suited (especially those exhibiting high and stable expression levels) for expression of GAD65 are selected, typically based on levels of GAD5 expressed and the GAD65 activity thereof, and then subcultured. A preferred method of assaying for high levels of GAD production is by protein blotting (Towbin et al., *Proc. Natl. Acad. Sci. USA* 76:4350–4354 (1979)) followed by immunostaining. While not wishing to be bound by theory, high levels of expression are likely to result from multicopy integration, wherein several copies of the transforming gene integrate into the host genome (see Romanos et al., *Yeast* 8:423–488 (1992)).

For production of GAD65 in large quantities according to the present invention, transformed cells which express GAD65 are typically grown in fermentors. For the large-scale production of recombinant DNA-based GAD65 in methylotrophic yeast, fed-batch or continuous culture may be employed. Typically a three-stage high cell density fed batch fermentation system is employed. In the first, or growth stage, the expression hosts are cultured in minimal defined medium with an excess of non-inducing carbon source (e.g., glycerol). When grown on such carbon sources, heterologous gene expression is repressed, which permits a cell mass to be generated in the absence of the GAD65. At this stage the pH of the medium is maintained at about pH 4.5 to 5.5, preferably about 5.0±0.1. A short period of non-inducing carbon source limitation is then used to further increase the cell mass and derepress the methanol responsive promoter. The pH of the medium during this stage is adjusted to the pH to be maintained during the production phase, which is generally carried out at a pH of about 4.5 to 5.5, preferably at a pH of about 5.0. Subsequent to the period of growth under limiting conditions, during the production stage methanol alone or a limiting amount of non-inducing carbon source plus methanol are added, inducing the expression of the GAD65 gene driven by a methanol responsive promoter.

Alternatively, for production scale culturing of *P. methanolica* fresh cultures of high producer clones are prepared in shake flasks. The resulting cultures are then used to inoculate culture medium in a fermenter. Typically, a 500 ml culture in YEPD grown at 30° C. for 1–2 days with vigorous agititation is used to inoculate a 5-liter fermenter. The cells are grown in a suitable medium containing salts, glucose, biotin, and trace elements at 28° C., pH 5.0, and >30% dissolved $O_2$. After the initial charge of glucose is consumed (as indicated by a decrease in oxygen consumption), a glucose/methanol feed is delivered into the vessel to induce production of the protein of interest. Because large-scale fermentation is carried out under conditions of limiting carbon, the presence of glucose in the feed does not repress the methanol-inducible promoter. The use of glucose in combination with methanol under glucose-limited conditions produces rapid growth, efficient conversion of carbon to biomass and rapid changes in physiological growth states, while still providing full induction of methanol-inducible gene promoters. In a typical fermentation run, a cell density of from about 80 to about 400 grams of wet cell paste per liter is obtained. "Wet cell paste" refers to the mass of cells obtained by harvesting the cells from the fermentor, typically by centrifugation of the culture.

Depending on the expression vector employed the GAD65 can be secreted into the culture medium and then purified, or if it is an intracellular protein it must be extracted from the yeast cells. In view of the number of sulfhydryl groups in GAD65, intracellular production is typically preferred. To extract GAD65 from the yeast, the cells are milled (typically using glass beads) or otherwise lysed, usually while keeping the cells chilled, e.g., at or below about 4–7° C. An extraction buffer adjusted to about pH 7.0 to 7.2 is employed that preferably contains protease inhibitors; reducing agents such as dithiothreitol or 2-mercaptoethanol; and a detergent, particularly a non-ionic detergent such as TRITON X-114 (polyethylene glycol tertiary octylphenyl ether), TRITON X-100 (polyethylene glycol mono [p-(1,1, 3,3-tetramethyl-butyl) phenyl] ether) (TRITON is a registered trademark of Union Carbide), at concentrations from about 0.5 to 20 volume/volume. This buffer, but without protease inhibitors, can also be used in subsequent purification steps.

Purification of GAD65 can be achieved by conventional chemical purification means, such as liquid chromatography, immunoaffinity chromatography, lectin affinity chromatography, gradient centrifugation, and gel electrophoresis, among others. Methods of protein purification are generally described in, e.g., Scopes, R., *Protein Purification*, Springer-Verlag, NY (1982), and for *P. pastoris* a general purification protocol is described in Clegg et al., *Bio/Technol.* 11:905–910 (1993), which are incorporated herein by reference. It is preferred that a reducing agent such as DTT or the like, a non-ionic detergent, and a phosphate buffering agent be present throughout most stages of the purification process to maintain stability of the purified GAD65.

In a preferred means for purification of GAD65 in active form, a series of purification steps are employed. As cellular extracts are typically heavily laden with particulate matter, a pre-purification or separation such as phase partitioning into an aqueous phase and detergent phase (containing the GAD65) is employed. Thus, the initial part of the purification process can be broadly summarized as preparing a crude cell extract (or cell fraction) containing GAD65, clarifying the extract (e.g., by centrifugation), and separating out the GAD65 by phase partitioning. For example, phase partitioning can be induced by raising the temperature to about 30° C., then centrifuging the extract and the detergent phase containing GAD65 is separated from the remaining aqueous phase. The aqueous phase can then be re-extracted as desired. See, Bordier, *J. Biol. Chem.* 256:1604–1607 (1981). An alternative method of phase partitioning is to adjust the extract to 1.0 M NaCl and apply it to a phenyl Sepharose® column to condense the detergent phase. GAD binds to the resin and can be eluted with water.

Following the preparation of an extract by phase partitioning, GAD65 is purified from the extract using a combination of anion exchange chromatography, cation exchange chromatography, and hydroxyapatite chromatography. GAD65 has been found to bind to anion exchange media, while contaminants preferentially bind to cation exchange media. GAD65 produced in methylotrophic yeasts is typically contaminated with alcohol oxidase, which is removed by anion exchange chromatography, in particular by chromatography on a strong anion exchanger (e.g., media having quaternary ammonium groups). A variety of ion exchange media are known in the art and are available from commercial suppliers. Such media are typically in the from of resin beads composed of dextran, cross-liked agarose, or similar materials. Ion exchange media are typically prepared in columns to which the material to be fractionated is applied as a solution.

Within the present invention it is preferred to first fractionate the extract using a weak anion exchanger, such as those containing DEAE (diethylaminoethyl) or QAE (quaternary aminoethyl) groups, although strong anion exchangers can also be employed. GAD65 binds to such media under conditions of very low ionic strength and can be eluted with higher ionic strength buffers (equivalent to about 50–200 mM NaCl). The GAD65-containing eluate is then applied to a cation exchange medium, such as one containing carboxymethyl or sulfopropyl groups, which preferentially binds contaminants. Subsequently, anion exchange chromatography, preferably using a strong anion exchanger, is used to remove alcohol oxidase. The GAD65-containing eluate from the second anion exchange step is then applied to hydroxyapatite, and the GAD65 is eluted with potassium phosphate. Particularly preferred embodiments of these fractionation steps are described in more detail below.

A preferred first anion exchange chromatography step employs DEAE (diethylaminoethyl) chromatography. The DEAE column (e.g., DEAE-Sepharose® Pharmacia Biotech, Piscataway, N.J.) is equilibrated with sample buffer and, before applying the detergent phase GAD65-containing sample to the column, sample may be diluted in buffer containing protease inhibitors and centrifuged at about 5° C. to remove particulate which may be present from the phase partitioning step. The diluted sample is then applied to the DEAE column, the column is washed with buffer, and GAD65 is then eluted with a saline-containing gradient (e.g., 0.8 M NaCl). GAD65 can be detected with GAD65-specific monoclonal antibody in Western blots (eluting as a broad band from 50–200 mM NaCl) and the GAD65 fractions pooled as desired.

Within a preferred embodiment of the invention purified GAD65 from a DEAE purification step is dialyzed against a buffer containing a reducing agent and detergent, such as DTT and Triton X-114, and further containing aminoethyl-isothiouroniumbromide hydrobromide, morpholinoethane-sulfonic acid, EDTA and protease inhibitors such as those present in the initial extraction process, at pH≧6.0, preferably about pH 6.0 to pH 6.4, more preferably about pH 6.2. The dialyzed GAD65 is then passed over a bed of S-Sepharose® or the like equilibrated in the same buffer. The GAD65 passes through the column during sample loading and the pass-through is collected.

The GAD65 pass-through from the S-Sepharose® column is applied to a Q-Sepharose® column or the equivalent. The S-Sepharose® GAD65 pass-through is adjusted to about pH 7.8 to 8.2, preferably about pH 8.0, and applied to a column of Q-Sepharose® equilibrated with a reducing agent and detergent at about pH 8.0 (e.g., buffer of 20 mM Tris, 20 mM MES, 20 mM MOPS, 5 mM EDTA, 1 mM DTT, 1 mM AET, 20 uM Pyridoxal phosphate, 0.2% Triton X-114, and 20 mM acetic acid, adjusted with NaOH to pH 8.0). The column is washed with the buffer and when the wash is terminated, a gradient is developed between the buffer pH 8.0 and the same buffer having a pH less than 5.7, preferably between about 3.5 and 5.0, more preferably about 4.26. Within an alternative embodiment pH gradients are developed using an eluant comprising a plurality of buffers having different pKs over the desired pH range. For example, a pH 8 to pH 5 gradient can be developed using a combination of buffers having pKs of approximately 8, 7, 6 and 5. Such a system allows development of a smooth gradient over a desired pH range. GAD65 elutes from the Q-Sepharose® at a pH of about 5.7, just before a highly chromogenic contaminant (alcohol oxidase) elutes. The GAD65-containing fractions are quickly adjusted to pH 7.0 and dialyzed against a phosphate buffer with a reducing agent and detergent (e.g., containing 10 mM potassium phosphate, 5 mM DTT, 5 mM EDTA, 1 mM AET, 20 uM pyridoxal phosphate, and 0.2% Triton X-114).

Hydroxyapatite chromatography is employed in a preferred GAD65 purification protocol. For example, in one embodiment the GAD65 from a pooled Q-Sepharose purification is loaded onto a column of hydroxyapatite equilibrated in substantially the same buffer as the dialyzed material from Q-Sepharose purification, e.g., a phosphate buffer, pH 7.0, containing a reducing agent and detergent. The bound GAD65 elutes with a phosphate salt, typically a gradient of potassium phosphate or sodium phosphate. GAD65 starts eluting almost immediately and the peak is typically followed by a long tail. This is substantially purified GAD.

In an alternative purification protocol, the first anion exchange step is employed as an early prepurification step prior to phase partitioning into detergent and aqueous fractions. Modifications to the procedure can also be used to increase the purity of the sample following the first anion exchange and prior to phase partitioning. One modification employs the addition of an in-series "post column" during the elution of the anion exchange bed. The post column can be ceramic hydroxyapatite (Bio-Rad Laboratories). A slight modification of the elution conditions enables GAD65 elution through both matrices while allowing further protein removal from the elution flow path by the post column. The modification to the elution condition involves augmenting the elution buffer to 0.4 M in ionic strength with potassium phosphate instead of NaCl. This modified elution buffer inhibits GAD65 binding to the hydroxyapatite matrix and removes contaminant proteins. The resultant decrease in total protein burden facilitates phase partitioning.

Upon inducing phase partitioning with elevated temperature the upper depleted phase and associated proteins may experience an increase in solvent activity ($H_2O$) which may cause the detergent soluble contaminants to drop out of the upper phase onto and/or into the phase interface. This may minimize the accurate and complete harvest of GAD65 in the lower phase by obscuring visualization of the phase interface as well as physically contaminating a portion of the condensed phase. To address this aspect a cold condensation method employing alternative detergent(s) can be used, for example a binary detergent system comprised of Triton X-114 and Triton X-45. By increasing the mole fraction of Triton X-45 the system can be forced to cloud/partition at temperatures as low as 0 to 5° C. and reduce the effect of contaminants dropping from the upper phase into the lower phase. Alternatively, the condensed TX-114 phase can be floated on top of the depleted phase by using 30% glycerol as well as the standard 2% TX-114 primary GAD buffer (PGB) system described below. The inclusion of 30% glycerol renders the detergent depleted phase more dense than the condensed Triton phase such that the latter becomes the upper phase, negating the effects of any fouling precipitation into the condensed phase. In another modification the Triton concentration is increased from 2% to 4% at this stage. The doubling of the Triton concentration prior to condensing doubles the volume of the condensed phase, thereby minimizing loss of GAD65 in the harvest as the same interface fouling occurs on a larger total volume of condensed phase, minimizing the fractional loss during collection of the lower phase. The increase in total condensed phase may increase the apparent transfer coefficient for GAD65, resulting in a more complete recovery of the available GAD65 at this step.

In an alternative purification protocol the cation exchange step described above may be omitted. The GAD65-containing detergent phase from the phase partitioning step is further purified by a second anion exchange chromatography step, followed by hydroxyapatite chromatography, as outlined above.

Prepared according to a preferred purification protocol, the GAD65 specific activity varies from at least about 0.12 units per mg to 0.47 units per mg or more (a unit of activity being uMoles $CO_2$ liberated per minute per mg of protein with radiolabeled glutamic acid as the substrate). Coomassie blue-stained gels show alpha and beta GAD bands, as well as trace levels of dimer and some degradation fragments of insignificant amounts.

Thus, as discussed above, the present invention provides recombinant GAD65 isolated from methylotrophic yeast. Purified GAD65 in large quantities and having high enzymatic activity is also provided. Substantially pure GAD65 of at least about 70–80% is preferred, at least about 90–95% more preferred, and 96–99% or more, to homogeneity, most preferred, particularly for pharmaceutical and diagnostic uses. Once purified, partially or to homogeneity, as desired, the recombinant GAD65 may then be used to generate antibodies, in assay procedures for anti-GAD65 autoantibodies, etc. Such procedures are described in, e.g., PCT publication WO 92/20811, incorporated herein by reference.

The following examples are offered by way of illustration, not by way of limitation.

EXAMPLE 1

Expression of GAD65 in *P. pastoris*

A *Pichia pastoris* GAD65 expression vector was constructed by subcloning a Sac I-Xba I GAD65 cDNA fragment (Karlsen et al., *Proc. Natl. Acad. Sci. USA*, 88:8337–8341 (1991)) into the plasmid pHIL-D2 (Invitrogen Corp., San Diego, Calif.). The GAD65 cDNA fragment was blunt-ended with T4 DNA polymerase and inserted into the (blunt-ended) Eco RI site of pHIL-D2. The resulting plasmid, designated pCZR65, was linearized by digestion with Not I, and 10 µg of plasmid was used to transform *P. pastoris* strain GS115 (His$^-$) (Invitrogen Corp.) to His$^+$ using the electroporation protocol specified by the supplier (Invitrogen Corp.).

His$^+$ colonies were plated on agar media containing methanol (1% methanol, 2% agar (Difco Laboratories, Detroit, Mich.), 1X yeast nitrogen base (Difco), 400 µg/ml biotin), overlaid with a nitrocellulose filter, and incubated at 30° C. for 48 hours. The nitrocellulose, which had yeast colonies adhering to it, was then treated with 0.2 N NaOH/ 1% SDS for 30 minutes to lyse the cells. The filter was then blocked with NFM-TTBS (5% nonfat milk powder in 20 mM Tris pH 7.5, 160 mM NaCl, 0.1% Tween 20), probed for one hour with GAD6 antibody, a monoclonal antibody specific for GAD65 (Chang and Gottlieb, *J. Neurosci.*, 8:2123–2130 (1988)), then probed for one hour with horseradish peroxidase-conjugated goat anti-rabbit polyclonal antisera (The Jackson Laboratory, Bar Harbor, Me.). A positive signal was visualized by enhanced chemiluminescence (Amersham Corp., Arlington Heights, Ill.) and autoradiography. Approximately 20% of the His$^+$ colonies were found to express GAD65.

Of several hundred colonies screened, 1–2% appeared to produce elevated levels of GAD65 as determined by the level of chemiluminescence in the immunoassay. Fourteen of these colonies were chosen for further analysis. These were cultured in 5 ml of minimal methanol broth (1X yeast nitrogen base (Difco), 400 µg/ml biotin, 1% methanol) or 5 ml of minimal glucose broth (1X yeast nitrogen base (Difco), 400 µg/ml biotin, 1% glucose) for 48 hours. Cells were harvested and disrupted with glass beads in lysis buffer (5% SDS, 8 M urea, 100 mM Tris pH 6.8, 2 mM EDTA, 10% glycerol). Protein concentration was measured by the method of Lowry et al. (*J. Biol. Chem.* 193:265–275 (1951)). One microgram of protein from each strain was electrophoresed on an SDS-polyacrylamide gel and transferred to nitrocellulose ("Western" blotting; Towbin et al., *Proc. Natl. Acad. Sci. USA*, 76:4350–4354 (1979)). Blots were developed with GAD6 antibody as described above. One strain, designated GAD4, made the highest levels of GAD65 and was chosen for further analysis.

For production of GAD65 by *P. pastoris* GAD4, the strain was grown as described above in non-inducing glucose (G) or inducing methanol (M). Ten µg total protein was electrophoresed on an SDS-polyacrylamide gel and stained with Coomassie brilliant blue. A similar gel loaded with 1 µg of total protein was blotted to nitrocellulose and probed with GAD6 antibody. The results demonstrated that methanol strongly induced the expression of GAD65 in this strain.

EXAMPLE 2

Purification of GAD65 from *P. pastoris*

To extract GAD65 from the yeast expressing GAD65 as described in Example 1, the yeast were milled in a DYNO-MILL while keeping chilled at or below 5° C. The extraction buffer contained protease inhibitors as well as the detergent Triton X-114. The buffer components were: 40 mM HEPES, 5 mM DTT, 5 mM EDTA, 20 µM Pyridoxal Phosphate (PL), 1 mM aminoethylisothiouroniumbromide hydrobromide (AET), 20% (w/v) precondensed Triton X-114, 25 µg/ml Aprotinin, 5 µg/ml Leupeptin, 5 µg/ml Pepstatin, and 0.1 mM PMSF. The buffer was adjusted to pH 7.2. This buffer, with 2% pre-condensed Triton X-114 but containing no protease inhibitors, was the primary buffer used in the subsequent chromatography steps, and is referred to herein as Standard GAD Buffer, or SGB.

The milled extract was heavily laden with particulate matter. Phase partitioning was induced by raising the sample temperature to 30° C. long enough to achieve a uniform temperature throughout the sample. The sample was then centrifuged at 4000×g for 10 minutes at 30°. The bottom oily phase containing GAD was siphoned out and the remaining aqueous phase was re-extracted. Re-extraction was performed by bringing the aqueous phase to 10% (w/v) pre-condensed Triton X-114 and taking it through the thermal cycle and centrifugation processes again. The second detergent phase containing GAD was combined with the first.

For DEAE chromatography, a 3 liter column of DEAE Sephadex® (Pharmacia Biotech) was used to accommodate the protein load resulting from the processing of one 5 liter fermentation. The column was equilibrated in SGB described above. Before applying the detergent phase GAD-containing sample, it was diluted 1:5 in SGB with protease inhibitors and centrifuged at 4000×g for 30 minutes at 5° C. This removed the particulate harvested during the phase partitioning step. The diluted, spun sample was then applied to the column at 20 ml/min. When loading was completed the column was washed with starting buffer (SGB). When the OD returned to baseline, a 9 liter gradient, formed between SGB and SGB containing 0.8 M NaCl, was initiated. The GAD65 (detected with GAD6 monoclonal antibody in Western blots) eluted as a broad band from 50–200 mM NaCl. Samples were assayed by Western blots and Coomassie blue-stained gels, and GAD65-containing fractions were pooled.

The pooled material from the DEAE step was prepared for cation exchange chromatography on S-Sepharose® by dialysis against a pH 6.2 buffer containing the following components: 5 mM MES (morpholinoethanesulfonic acid); 5 mM EDTA; 5 mM dithiothreitol (DTT); 1 mM AET; 0.2% Triton X-114; and the protease inhibitors present in the initial milling process described above, at their respective concentrations.

The conductivity of the dialyzed protein was approximately 1 milliSeimen. The protein was then passed, at 25.4 cm/hr, over a bed of S-Sepharose® previously equilibrated in the same buffer. This step was a "negative binding" step as GAD65 passes through the column during sample loading. The "pass-through" was collected and saved.

The pass-through from the S-Sepharose® column was prepared for Q-Sepharose® chromatography by adjusting to 20 mM Tris and carefully adjusting the pH with 2N NaOH to pH 8.0. The conductivity of this material was approximately 2.35 milliSeimens. A 220 ml column of Q-sepharose was packed and equilibrated in the following buffer: Buffer A: pH=8.0; 20 mM Tris; 20 mM MES; 20 mM MOPS; 5 mM EDTA; 1 mM DTT; 1 mM AET; 20 uM Pyridoxal phosphate (PL); 0.2% Triton X-114; and 20 mM acetic acid. This buffer was adjusted with NaOH to pH 8.0, and had a conductivity of 4.5 milliSeimens.

The GAD solution was then loaded onto the Q-Sepharose® column. Following the load, the column was washed with 250 mL of Buffer A. When the wash was terminated, a 2L gradient was developed between Buffer A (pH=8.0) and Buffer B (Buffer A but having a pH of 4.26). GAD eluted from the Q-Sepharose® at a pH of about 5.7, just before a highly chromogenic contaminant (alcohol oxidase) eluted. The GAD containing fractions were quickly adjusted to pH 7.0, and in preparation for the final step of the purification the fractions were dialyzed against a buffer containing 10 mM potassium phosphate, 5 mM DTT, 5 mM EDTA, 1 mM AET, 20 uM pyridoxal phosphate, and 0.2% Triton X-114. Speed at this point was important as the concentrated GAD eluting from the Q-Sepharose® appeared unstable, and phosphate appeared to have a stabilizing effect.

For hydroxyapatite chromatography, the dialyzed material from the pooled Q-Sepharose® step was loaded onto a 100 ml column of hydroxyapatite equilibrated in the same buffer as the dialyzed material from the Q-Sepharose® step. The bound GAD65 was eluted with a gradient of potassium phosphate formed between 250 ml of 10 mM potassium phosphate, 5 mM DTT, 5 mM EDTA, 1 mM AET, 20 $\mu$M pyridoxal phosphate, and 0.2% Triton X-114, pH 6.8; and 250 ml of the same buffer containing 150 mM potassium phosphate. GAD65 started eluting almost immediately, and the peak was followed by a long tail. This was substantially purified GAD. Prepared as such, the enzyme specific activity varied from 0.12 units per mg to 0.47 units per mg (a unit of activity being $\mu$moles $CO_2$ liberated per minute per mg of protein with radiolabeled glutamic acid as the substrate). Coomassie blue-stained gels showed the alpha and beta GAD bands as well as trace levels of dimer and some degradation fragments of insignificant amounts.

The enzymatic activity of GAD65 was assayed using the method of Wu et al., *Methods Enzymol.* 113:3–11 (1985). To a 1.5 ml tube was added 21 $\mu$l of cold glutamic acid stock solution (5 mM in assay buffer), 8 $\mu$l of L-(1-$^{14}$C) glutamic acid (Amersham Corp., Arlington Heights, Ill.), 71 $\mu$l of assay buffer (50 mM potassium phosphate pH 7.2, 5 mM dithiothreitol, 1% Triton X-114, 1 mM 1-aminoethylisothiouronium bromide (Sigma Chemical Co., St. Louis, Mo.), and 0.2 mM pyridoxal phosphate (Sigma)). The reaction was initiated by adding 50 $\mu$l of sample in assay buffer (pre-equilibrated to 37° C.). 50 $\mu$l of hyamine base (Packard Instrument Co., Meriden, Conn.) was pipetted into a filter disk (Whatman, Inc., Clifton, N.J.) that was placed in the cap of the tube. The tube was then capped and incubated for two hr at 37° C., then for 60 min at 4° C. The filters were transferred to 2 ml of scintillation liquid (Ultima Gold™, Packard Instrument Co.) and counted in a beta counter (Tri-carb® 4530, Packard Instrument Co.). Samples were diluted so as to be in the linear range of a standard curve prepared using known amounts of GAD. One enzyme unit was defined as 1 $\mu$mole of product formed per min at 37° C. Results (Table 1) were adjusted by a conversion factor determined from the ratio of total glutamate in the assay to radiolabeled glutamate in the assay.

TABLE 1

| Step | Total Protein (grams) | Activity (cpm) | Step Re-covery | cpm/g | Fold Purifi-cation |
| --- | --- | --- | --- | --- | --- |
| Total Extract | 114 | $1.74 \times 10^{11}$ | — | $1.59 \times 10^9$ | 1 |
| Phase partition | 10.2 | $8 \times 10^{10}$ | 47% | $7.8 \times 10^9$ | 5.2 |
| DEAE | 4.7 | $8 \times 10^{10}$ | 100% | $1.7 \times 10^{10}$ | 11.3 |
| S | 3.16 | $6.13 \times 10^{10}$ | 76% | $1.9 \times 10^{10}$ | 12.6 |
| Q | 0.5 | $3.79 \times 10^{10}$ | 62% | $7.5 \times 10^{10}$ | 50 |
| HAP | 0.402 | $2.9 \times 10^{10}$ | 76% | $7.2 \times 10^{10}$ | 48 |

EXAMPLE 3

Expression of GAD65 in *P. methanolica*

A. *P. methanolica* cells (strain CBS6515 from American Type Culture Collection, Rockville, Md.) were mutagenized by UV exposure. A killing curve was first generated by plating cells onto several plates at approximately 200–250 cells/plate. The plates were then exposed to UV radiation using a G8T5 germicidal lamp (Sylvania) suspended 25 cm from the surfaces of the plates for periods of time as shown in Table 2. The plates were then protected from visible light sources and incubated at 30° C. for two days.

TABLE 2

| | Viable Cells | | |
| --- | --- | --- | --- |
| Time | Plate 1 | Plate 2 | Average |
| 0 sec. | 225 | 229 | 227 |
| 1 sec. | 200 | 247 | 223 |
| 2 sec. | 176 | 185 | 181 |
| 4 sec. | 149 | 86 | 118 |
| 8 sec. | 20 | 7 | 14 |
| 16 sec. | 0 | 2 | 1 |

Large-scale mutagenesis was then carried out using a 2-second UV exposure to provide about 20% killing. Cells were plated at approximately $10^4$ cells/plate onto eight YEPD (Table 3) plates that were supplemented with 100 mg/L each of uracil, adenine, and leucine, which were added to supplement the growth of potential auxotrophs having the cognate deficiencies. (The preparation of *P. methanolica* auxotrophic mutants is also described in commonly owned application Ser. No. 08/703,808, filed Aug. 26, 1996, U.S. Pat. No. 5,736,383 incorporated by reference herein.) Following UV exposure the plates were wrapped in foil and incubated overnight at 30° C. The following day the colonies on the plates (~$10^5$ total) were resuspended in water and washed once with water. An amount of cell suspension sufficient to give an $OD_{600}$ of 0.1–0.2 was used to inoculate 500 ml of minimal broth made with yeast nitrogen base without amino acids or ammonia, supplemented with 1% glucose and 400 g/L biotin. The culture was placed in a 2.8 L baffled Bell flask and shaken vigorously overnight at 30° C. The following day the cells had reached an $OD_{600}$ of ~1.0–2.0. The cells were pelleted and resuspended in 500 ml of minimal broth supplemented with 5 g/L ammonium sulfate. The cell suspension was placed in a 2.8 L baffled Bell flask and shaken vigorously at 30° C. for 6 hours. 50 ml of the culture was set aside in a 250-ml flask as a control, and to the remainder of the culture was added 1 mg nystatin (Sigma Chemical Co., St. Louis, Mo.) to select for auxotrophic mutants (Snow, *Nature* 211:206–207, 1966). The cultures were incubated with shaking for an additional hour. The control and nystatin-treated cells were then harvested by centrifugation and washed with water three times. The washed cells were resuspended to an $OD_{600}$ of 1.0 in 50% glycerol and frozen. Titering of nystatin-treated cells versus the control cells for colony forming units revealed that nystatin enrichment had decreased the number of viable cells by a factor of $10^4$.

TABLE 3

YEPD

2% D-glucose
2% Bacto ™ Peptone (Difco Laboratories, Detroit, MI)
1% Bacto ™ yeast extract (Difco Laboratories)
0.004% adenine
0.006% L-leucine

ADE D 0.056% -Ade -Trp -Thr powder
0.67% yeast nitrogen base without amino acids
2% D-glucose
0.5% 200X tryptophan, threonine solution

ADE DS 0.056% -Ade -Trp -Thr powder
0.67% yeast nitrogen base without amino acids
2% D-glucose
0.5% 200X tryptophan, threonine solution
18.22% D-sorbitol

LEU D 0.052% -Leu -Trp -Thr powder
0.67% yeast nitrogen base without amino acids
2% D-glucose
0.5% 200X tryptophan, threonine solution

HIS D 0.052% -His -Trp -Thr powder
0.67% yeast nitrogen base without amino acids
2% D-glucose
0.5% 200X tryptophan, threonine solution

URA D 0.056% -Ura -Trp -Thr powder
0.67% yeast nitrogen base without amino acids TABLE 3-continued 2% D-glucose
0.5% 200X tryptophan, threonine solution

URA DS 0.056% -Ura -Trp -Thr powder
0.67% yeast nitrogen base without amino acids
2% D-glucose
0.5% 200X tryptophan, threonine solution
18.22% D-sorbitol -Leu -Trp -Thr powder powder made by combining 4.0 g adenine, 3.0 g arginine, 5.0 g aspartic acid, 2.0 g histidine, 6.0 g isoleucine, 4.0 g lysine, 2.0 g methionine, 6.0 g phenylalanine, 5.0 g serine, 5.0 g tyrosine, 4.0 g uracil, and 6.0 g valine, (all L- amino acids)

-His -Trp -Thr powder powder made by combining 4.0 g adenine, 3.0 g arginine, 5.0 g aspartic acid, 6.0 g isoleucine, 8.0 g leucine, 4.0 g lysine, 2.0 g methionine, 6.0 g phenylalanine, 5.0 g serine, 5.0 g tyrosine, 4.0 g uracil, and 6.0 g valine (all L- amino acids)

-Ura -Trp -Thr powder powder made by combining 4.0 g adenine, 3.0 g arginine, 5.0 g aspartic acid, 2.0 g histidine, 6.0 g isoleucine, 8.0 g leucine, 4.0 g lysine, 2.0 g methionine, 6.0 g phenylalanine, 5.0 g serine, 5.0 g tyrosine, and 6.0 g valine (all L- amino acids)

-Ade -Trp -Thr powder powder made by combining 3.0 g arginine, 5.0 g aspartic acid, 2.0 g histidine, 6.0 g isoleucine, 8.0 g leucine, 4.0 g lysine, 2.0 g methionine, 6.0 g phenylalanine, 5.0 g serine, 5.0 g tyrosine, 4.0 g uracil, and 6.0 g valine (all L- amino acids)

200X tryptophan, threonine solution 3.0% L-threonine, 0.8% L-tryptophan in $H_2O$
For plates, add 1.8% Bacto ™ agar (Difco Laboratories)

$10^{-2}$ dilutions of nystatin-treated cells were plated on 15 YEPD plates. Colonies were replica-plated onto minimal plates (2% agar, 1×YNB, 2% glucose, 400 g/L biotin). The frequency of auxotrophs was about 2–4%. Approximately 180 auxotrophic colonies were picked to YEPD+Ade, Leu, Ura plates and replica-plated to various dropout plates. All of the auxotrophs were Ade⁻. Of these, 30 were noticably pink on dropout plates (LEU D, HIS D, etc.; see Table 3). Of the 30 pink mutants, 21 were chosen for further study; the remainder were either leaky for growth on ADE D plates or contaminated with wild-type cells.

The Ade⁻ mutants were then subjected to complementation analysis and phenotypic testing. To determine the number of loci defined by the mutants, all 21 mutants were mated to a single pink, Ade⁻ tester strain (strain #2). Mating was carried out by mixing cell suspensions ($OD_{600}$=1) and plating the mixtures in 10 l aliquots on YEPD plates. The cells were then replicated to SPOR media (0.5% Na acetate, 1% KCl, 1% glucose, 1% agar) and incubated overnight at 30° C. The cells were then replica-plated to ADE D plates for scoring of phenotype. As shown in Table 3, some combinations of mutants failed to give Ade⁺ colonies (possibly defining the same genetic locus as in strain #2), while others gave rise to numerous Ade⁺ colonies (possibly defining a separate genetic locus). Because mutant #3 gave Ade⁺ colonies when mated to #2, complementation testing was repeated with mutant #3. If the group of mutants defined two genetic loci, then all mutants that failed to give Ade⁺ colonies when mated to strain #2 should give Ade⁺ colonies when mated to #3. Results of the crosses are shown in Table 4.

TABLE 4

| Mutant | x Mutant #2 | x Mutant #3 |
|---|---|---|
| 1# | + | − |
| 3# | + | − |
| #10 | + | − |
| #15 | + | − |
| #18 | + | − |
| #24 | + | − |
| #28 | + | − |
| #30 | + | − |
| #2 | − | + |
| #6 | − | + |
| #8 | − | + |
| #9 | − | + |
| #11 | − | + |
| #17 | − | + |
| #19 | − | + |
| #20 | − | + |
| #22 | − | + |
| #27 | − | + |
| #4 | + | + |
| #12 | + | + |
| #16 | + | + |

As shown in Table 4, most mutants fell into one of two groups, consistent with the idea that there are two adenine biosynthetic genes that, when missing, result in pink colonies on limiting adenine media. Three colonies (#4, #12, and #16) may either define a third locus or exhibit intragenic complementation. Two intensely pigmented mutants from each of the two complementation groups (#3 and #10; #6 and #11) were selected for further characterization. Additional analysis indicated that Ade⁻ was the only auxotrophy present in these strains.

A *P. methanolica* clone bank was constructed in the vector pRS426, a shuttle vector comprising 2 μ and *S. cerevisiae* URA3 sequences, allowing it to be propagated in *S. cerevisiae*. Genomic DNA was prepared from strain CBS6515 according to standard procedures. Briefly, cells were cultured overnight in rich media, spheroplasted with zymolyase, and lysed with SDS. DNA was precipitated from the lysate with ethanol and extracted with a phenol/chloroform mixture, then precipitated with ammonium acetate and ethanol. Gel electrophoresis of the DNA preparation showed the presence of intact, high molecular weight DNA and appreciable quantities of RNA. The DNA was partially digested with Sau 3A by incubating the DNA in the presence of a dilution series of the enzyme. Samples of the digests were analyzed by electrophoresis to determine the size distribution of fragments. DNA migrating between 4 and 12 kb was cut from the gel and extracted from the gel slice. The size-fractionated DNA was then ligated to pRS426 that had been digested with Bam HI and treated with alkaline phosphatase. Aliquots of the reaction mixture were electroporated in *E. coli* MC1061 cells using a BioRad Gene Pulser device as recommended by the manufacturer.

The genomic library was used to transform *S. cerevisiae* strain HBY21A (ade2 ura3) by electroporation (Becker and Guarente, *Methods Enzymol.* 194:182–187, 1991). The cells were resuspended in 1.2 M sorbitol, and six 300 μl aliquots were plated onto ADE D, ADE DS, URA D and URA DS plates (Table 3). Plates were incubated at 30° C. for 4–5 days. No Ade⁺ colonies were recovered on the ADE D or ADE DS plates. Colonies from the URA D and URA DS plates were replica-plated to ADE D plates, and two closely spaced, white colonies were obtained. These colonies were restreaked and confirmed to be Ura⁺ and Ade⁺. These two strains, designated Ade1 and Ade6, were streaked onto media containing 5 FOA (5 fluoro orotic acid; Sikorski and Boeke, *Methods Enzymol.* 194:302–318). Ura⁻ colonies were obtained, which were found to be Ade⁻ upon replica plating. These results indicate that the Ade⁺ complementing activity is genetically linked to the plasmid-borne URA3 marker. Plasmids obtained from yeast strains Ade1 and Ade6 appeared to be identical by restriction mapping as described below. These genomic clones were designated pADE1-1 and pADE1-G, respectively.

Total DNA was isolated from the HBY21A transformants Ade1 and Ade6 and used to transform *E. coli* strain MC1061 to Amp®. DNA was prepared from 2 Amp® colonies of Ade1 and 3 Amp® colonies of Ade6. The DNA was digested with Pst I, Sca I, and Pst I+Sca I and analyzed by gel electrophoresis. All five isolates produced the same restriction pattern.

PCR primers were designed from the published sequence of the *P. methanolica* ADE2 gene (also known as ADE1; Hiep et al., *Yeast* 9:1251–1258, 1993). Primer 9080 (SEQ ID NO:3) was designed to prime at bases 406–429 of the ADE2 DNA (SEQ ID NO:1), and primer 9079 (SEQ ID NO:4) was designed to prime at bases 2852–2829. Both primers included tails to introduce Avr II and Spe I sites at each end of the amplified sequence. The predicted size of the resulting PCR fragment was 2450 bp.

PCR was carried out using plasmid DNA from the five putative ADE2 clones as template DNA. The 100 μl reaction mixtures contained 1×Taq PCR buffer (Boehringer Mannheim, Indianapolis, Ind.), 10–100 ng of plasmid DNA, 0.25 mM dNTPs, 100 pmol of each primer, and 1 μl Taq polymerase (Boehringer Mannheim). PCR was run for 30 cycles of 30 seconds at 94° C., 60 seconds at 50° C., and 120 seconds at 72° C. Each of the five putative ADE2 genomic clones yielded a PCR product of the expected size (2.4 kb). Restriction mapping of the DNA fragment from one reaction gave the expected size fragments when digested with Bgl II or Sal I.

The positive PCR reactions were pooled and digested with Spe I. Vector pRS426 was digested with Spe I and treated with calf intestinal phosphatase. Four μl of PCR fragment and 1 μl of vector DNA were combined in a 10 μl reaction mix using conventional ligation conditions. The ligated DNA was analyzed by gel electrophoresis. Spe I digests were analyzed to identify plasmids carrying a subclone of the ADE2 gene within pRS426. The correct plasmid was designated pCZR118.

Because the ADE2 gene in pCZR118 had been amplified by PCR, it was possible that mutations that disabled the functional character of the gene could have been generated. To test for such mutations, subclones with the desired insert were transformed singly into *Saccharomyces cerevisiae* strain HBY21A. Cells were made electrocompetent and transformed according to standard procedures. Transformants were plated on URA D and ADE D plates. Three phenotypic groups were identified. Clones 1, 2, 11, and 12 gave robust growth of many transformants on ADE D. The transformation frequency was comparable to the frequency of Ura⁺ transformants. Clones 6, 8, 10, and 14 also gave a high efficiency of transformation to both Ura⁺ and Ade⁺, but the Ade⁺ colonies were somewhat smaller than those in the first group. Clone 3 gave many Ura⁺ colonies, but no Ade⁺ colonies, suggesting it carried a non-functional ade2 mutation. Clones 1, 2, 11, and 12 were pooled.

To identify the *P. methanolica* ade2 complementation group, two representative mutants from each complementation group (#3 and #10; #6 and #11), which were selected on the basis of deep red pigmentation when grown on limiting adenine, were transformed with the cloned ADE gene. Two hundred ml cultures of early log phase cells were harvested by centrifugation at 3000×g for 3 minutes and resuspended in 20 ml of fresh KD buffer (50 mM potassium phosphate buffer, pH 7.5, containing 25 mM DTT). The cells were incubated in this buffer at 30° C. for 15 minutes. The cells were then harvested and resuspended in 200 ml of ice-cold STM (270 mM sucrose, 10 mM Tris, pH 7.5, 1 mM $MgCl_2$). The cells were harvested and resuspended in 100 ml of ice-cold STM. The cells were again harvested and resuspended in 3–5 ml of ice-cold STM. 100 μl aliquots of electrocompetent cells from each culture were then mixed with Not I-digested pADE1-1 DNA. The cell/DNA mixture was placed in a 2 mm electroporation cuvette and subjected to a pulsed electric field of 5 kV/cm using a BioRad Gene Pulser™ set to 1000 Ω resistance and capacitance of 25 μF. After being pulsed, the cells were diluted by addition of 1 ml YEPD and incubated at 30° C. for one hour. The cells were then harvested by gentle centrifugation and resuspended in 400 μl minimal selective media lacking adenine (ADE D). The resuspended samples were split into 200 μl aliqouts and plated onto ADE D and ADE DS plates. Plates were incubated at 30° C. for 4–5 days. Mutants #6 and #11 gave $Ade^+$ transformants. No $Ade^+$ transformants were observed when DNA was omitted, hence the two isolates appeared to define the ade2 complementation group. The ADE2 sequence is shown in SEQ ID NO:1.

B. The *P. methanolica* clone bank disclosed in Section A was used as a source for cloning the Alcohol Utilization Gene (AUG1). The clone bank was stored as independent pools, each representing about 200–250 individual genomic clones. 0.1 μl of "miniprep" DNA from each pool was used as a template in a polymerase chain reaction with PCR primers (8784, SEQ ID NO:5; 8787, SEQ ID NO:6) that were designed from an alignment of conserved sequences in alcohol oxidase genes from *Hansenula polymorpha*, *Candida boidini*, and *Pichia pastoris*. The amplification reaction was run for 30 cycles of 94° C., 30 seconds; 50°0 C., 30 seconds; 72° C., 60 seconds; followed by a 7 minute incubation at 72° C. One pool (#5) gave a ~600 bp band. DNA sequencing of this PCR product revealed that it encoded an amino acid sequence with ~70% sequence identity with the *Pichia pastoris* alcohol oxidase encoded by the AOX1 gene and about 85% sequence identity with the *Hansenula polymorpha* alcohol oxidase encoded by the MOX1 gene. The sequence of the cloned AUG1 gene is shown in SEQ ID NO:2.

Sub-pools of pool #5 were analyzed by PCR using the same primers used in the initial amplification. One positive sub-pool was further broken down to identify a positive colony. This positive colony was streaked on plates, and DNA was prepared from individual colonies. Three colonies gave identical patterns after digestion with Cla I.

Restriction mapping of the genomic clone and PCR product revealed that the AUG1 gene lay on a 7.5 kb genomic insert and that sites within the PCR fragment could be uniquely identified within the genomic insert. Because the orientation of the gene within the PCR fragment was known, the latter information provided the approximate location and direction of transcription of the AUG1 gene within the genomic insert. DNA sequencing within this region revealed a gene with very high sequence similarity at the amino acid level to other known alcohol oxidase genes.

C. ade2 mutant *P. methanolica* cells are transformed by electroporation essentially as disclosed above with an expression vector comprising the AUG1 promoter and terminator, human GAD65 DNA (Karlsen et al., *Proc. Natl. Acad. Sci. USA* 88:8337–8341, 1991), and ADE2 selectable marker. Colonies are patched to agar minimal methanol plates (10 to 100 colonies per 100-mm plate) containing 20 g/L Bacto-agar (Difco), 6.7 g/L yeast nitrogen base without amino acids (Difco), 10 g/L methanol, and 0.4 μg/L biotin. The agar is overlayed with nitrocellulose, and the plates are inverted over lids containing 1 ml of 50% methanol in water and incubated for 3 to 5 days at 30° C. The membrane is then transferred to a filter soaked in 0.2 M NaOH, 0.1% SDS, 35 mM dithiothreitol to lyse the adhered cells. After 30 minutes, cell debris is rinsed from the filter with distilled water, and the filter is neutralized by rinsing it for 30 minutes in 0.1 M acetic acid.

The filters are then assayed for adhered protein. Unoccupied binding sites are blocked by rinsing in TTBS-NFM (20 mM Tris pH 7.4, 0.1% Tween 20, 160 mM NaCl, 5% powdered nonfat milk) for 30 minutes at room temperature. The filters are then transferred to a solution containing GAD6 monoclonal antibody (Chang and Gottlieb, *J. Neurosci.* 8:2123–2130, 1988), diluted 1:1000 in TTBS-NFM. The filters are incubated in the antibody solution with gentle agitation for at least one hour, then washed with TTBS (20 mM Tris pH 7.4, 0.1% Tween 20, 160 mM NaCl) two times for five minutes each. The filters are then incubated in goat anti-mouse antibody conjugated to horseradish peroxidase (1 mg/ml in TTBS-NFM) for at least one hour, then washed three times, 5 minutes per wash with TTBS. The filters are then exposed to commercially available chemiluminescence reagents (ECL; Amersham Inc., Arlington Heights, Ill.). Light generated from positive patches is detected on X-ray film.

To more accurately detect the level of $GAD_{65}$ expression, candidate clones are cultured in shake flask cultures. Colonies are grown for two days on minimal methanol plates at 30° C. as disclosed above. The colonies are used to inoculate 20 ml of minimal methanol media (6.7 g/L yeast nitrogen base without amino acids, 10 g/L methanol, 0.4 μg/L biotin) at a cell density of $1\times10^6$ cells/ml. The cultures are grown for 1–2 days at 30° C. with vigorous shaking. 0.2 ml of 50% methanol is added to each culture daily. Cells are harvested by centrifugation and suspended in ice-cold lysis buffer (20 mM Tris pH 8.0, 40 mM NaCl, 2 mM PMSF, 1 mM EDTA, 1 μg/ml leupeptin, 1 μg/ml pepstatin, 1 μg/ml aprotinin) at 10 ml final volume per 1 g cell paste. 2.5 ml of the resulting suspension is added to 2.5 ml of 400–600 micron, ice-cold, acid-washed glass beads in a 15-ml vessel, and the mixture is vigorously agitated for one minute, then incubated on ice for 1 minute. The procedure is repeated until the cells have been agitated for a total of five minutes. Large debris and unbroken cells are removed by centrifugation at 1000×g for 5 minutes. The clarified lysate is then decanted to a clean container. The cleared lysate is diluted in sample buffer (5% SDS, 8 M urea, 100 mM Tris pH 6.8, 10% glycerol, 2 mM EDTA, 0.01% bromphenol glue) and electrophoresed on a 4–20% acrylamide gradient gel (Novex, San Diego, Calif.). Proteins are blotted to nitrocellulose and detected with GAD6 antibody as disclosed above.

Clones exhibiting the highest levels of methanol-induced expression of foreign protein in shake flask culture are more extensively analyzed under high cell density fermentation conditions. Cells are first cultivated in 0.5 liter of YEPD broth at 30° C. for 1–2 days with vigorous agitation, then used to inoculate a 5-liter fermentation apparatus (e.g., BioFlow III; New Brunswick Scientific Co., Inc., Edison, N.J.). The fermentation vessel is first charged with mineral salts by the addition of 57.8 g $(NH_4)_2SO_4$, 68 g $KH_2PO_4$, 30.8 g $MgSO_4.7H_2O$, 8.6 g $CaSO_4.2H_2O$, 2.0 g NaCl, and 10 ml antifoam (PPG). $H_2O$ is added to bring the volume to 2.5 L, and the solution is autoclaved 40 minutes. After cooling, 350 ml of 50% glucose, 250 ml 10×trace elements (Table 5), 25 ml of 200 μg/ml biotin, and 250 ml cell inoculum are added.

TABLE 5

| 10 X trace elements: | | |
|---|---|---|
| $FeSO_4.7H_2O$ | 100 mM | 27.8 g/L |
| $CuSO_4.5H_2O$ | 2 mM | 0.5 g/L |
| $ZnCl_2$ | 8 mM | 1.09 g/L |
| $MnSO_4.H_2O$ | 8 mM | 1.35 g/L |
| $CoCl_2.6H_2O$ | 2 mM | 0.48 g/L |
| $Na_2MoO_4.2H_2O$ | 1 mM | 0.24 g/L |
| $H_3BO_3$ | 8 mM | 0.5 g/L |
| KI | 0.5 mM | 0.08 g/L |
| biotin | | 5 mg/L |
| thiamine | | 0.5 g/L |

Add 1–2 mls $H_2SO_4$ per liter to bring compounds into solution.

The fermentation vessel is set to run at 28° C., pH 5.0, and >30% dissolved $O_2$. The cells will consume the initial charge of glucose, as indicated by a sharp demand for oxygen during glucose consumption followed by a decrease in oxygen consumption after glucose is exhausted. After exhaustion of the initial glucose charge, a glucose-methanol feed supplemented with $NH_4^+$ and trace elements is delivered into the vessel at 0.2i (w/v) glucose, 0.2% (w/v) methanol for 5 hours followed by 0.1% (w/v) glucose, 0.4% (w/v) methanol for 25 hours. A total of 550 grams of methanol is supplied through one port of the vessel as pure methanol using an initial delivery rate of 12.5 ml/hr and a final rate of 25 ml/hr. Glucose is supplied through a second port using a 700 ml solution containing 175 grams glucose, 250 ml 10×trace elements, and 99 g $(NH_4)_2SO_4$. Under these conditions the glucose and methanol are simultaneously utilized, with the induction of $GAD_{65}$ expression upon commencement of the glucose-methanol feed. Cells from the fermentation vessel are analyzed for $GAD_{65}$ expression as described above for shake flask cultures.

Cells are removed from the fermentation vessel at certain time intervals and subsequently analyzed. Little $GAD_{65}$ expression is observed during growth on glucose. Exhaustion of glucose leads to low level expression of the $GAD_{65}$ protein; expression is enhanced by the addition of MeOH during feeding of the fermentation culture. The addition of methanol has a clear stimulatory effect of the expression of human $GAD_{65}$ driven by the methanol-responsive AUG1 promoter.

D. Transformation conditions were investigated to determine the electric field conditions, DNA topology, and DNA concentration that were optimal for efficient transformation of *P. methanolica*. All experiments used *P. methanolica* ade2 strain #11. Competent cells were prepared as previously described. Electroporation was carried out using a BioRad Gene Pulser™.

Three field parameters influence transformation efficiency by electroporation: capacitance, field strength, and pulse duration. Field strength is determined by the voltage of the electric pulse, while the pulse duration is determined by the resistance setting of the instrument. Within this set of experiments, a matrix of field strength settings at various resistances was examined. In all experiments, the highest capacitance setting (25 μF) of the instrument was used. 100 μl aliquots of electrocompetent cells were mixed on ice with 10 μl of DNA that contained approximately 1 μg of the ADE2 plasmid pCZR133 that had been linearized with the restriction enzyme Not I. Cells and DNA were transferred to 2 mm electroporation cuvettes (BTX Corp., San Diego, Calif.) and electropulsed at field strengths of 0.5 kV (2.5 kV/cm), 0.75 kV (3.75 kV/cm), 1.0 kV (5.0 kV/cm), 1.25 kV (6.25 kV/cm), and 1.5 kV (7.5 kV/cm). These field strength conditions were examined at various pulse durations. Pulse duration was manipulated by varying the instrument setting resistances to 200 ohms, 600 ohms, or "infinite" ohms. Pulsed cells were suspended in YEPD and incubated at 30° C. for one hour, harvested, resuspended, and plated. Three separate sets of experiments were conducted. In each set, electroporation conditions of 0.75 kV (3.75 kV/cm) at a resistance of "infinite" ohms was found to give a dramatically higher transformation efficiency than other conditions tested (see FIG. 1).

After the optimal pulse conditions were established, the influence of DNA topology on transformation efficiency was investigated. Electrocompetent cells were mixed with 1 μg of uncut, circular pCZR133 or with 1 μg of Not I-digested pCZR133. In three separate experiments, an average of roughly 25 transformants were recovered with circular DNA while linear DNA yielded an average of nearly $1\times10^4$ transformants. These data indicate that linear DNA transforms *P. methanolica* with much greater efficiency than circular DNA.

Finally, the relationship between DNA concentration and transformation efficiency was investigated. Aliquots of linear pCZR133 DNA (1 ng, 10 ng, 100 ng and 1 μg in 10 μl $H_2O$) were mixed with 100 μl electrocompetent cells, and electroporation was carried out at 3.75 kV/cm and "infinite" ohms. The number of transformants varied from about 10 (1 ng DNA) to $10^4$ (1 μg DNA) and was found to be proportional to the DNA concentration.

E. Integration of transforming DNA into the genome of *P. methanolica* was detected by comparison of DNA from wild-type cells and stable, white transformant colonies. Two classes of integrative transformants were identified. In the first, transforming DNA was found to have integrated into a homologous site. In the second class, transforming DNA was found to have replaced the endogenous AUG1 open reading frame. While not wishing to be bound by theory, this second transformant is believed to have arisen by a "transplacement recombination event" (Rothstein, *Methods Enzymol.* 194:281–301, 1991) whereby the transforming DNA replaces the endogenous DNA via a double recombination event.

Figure 2:
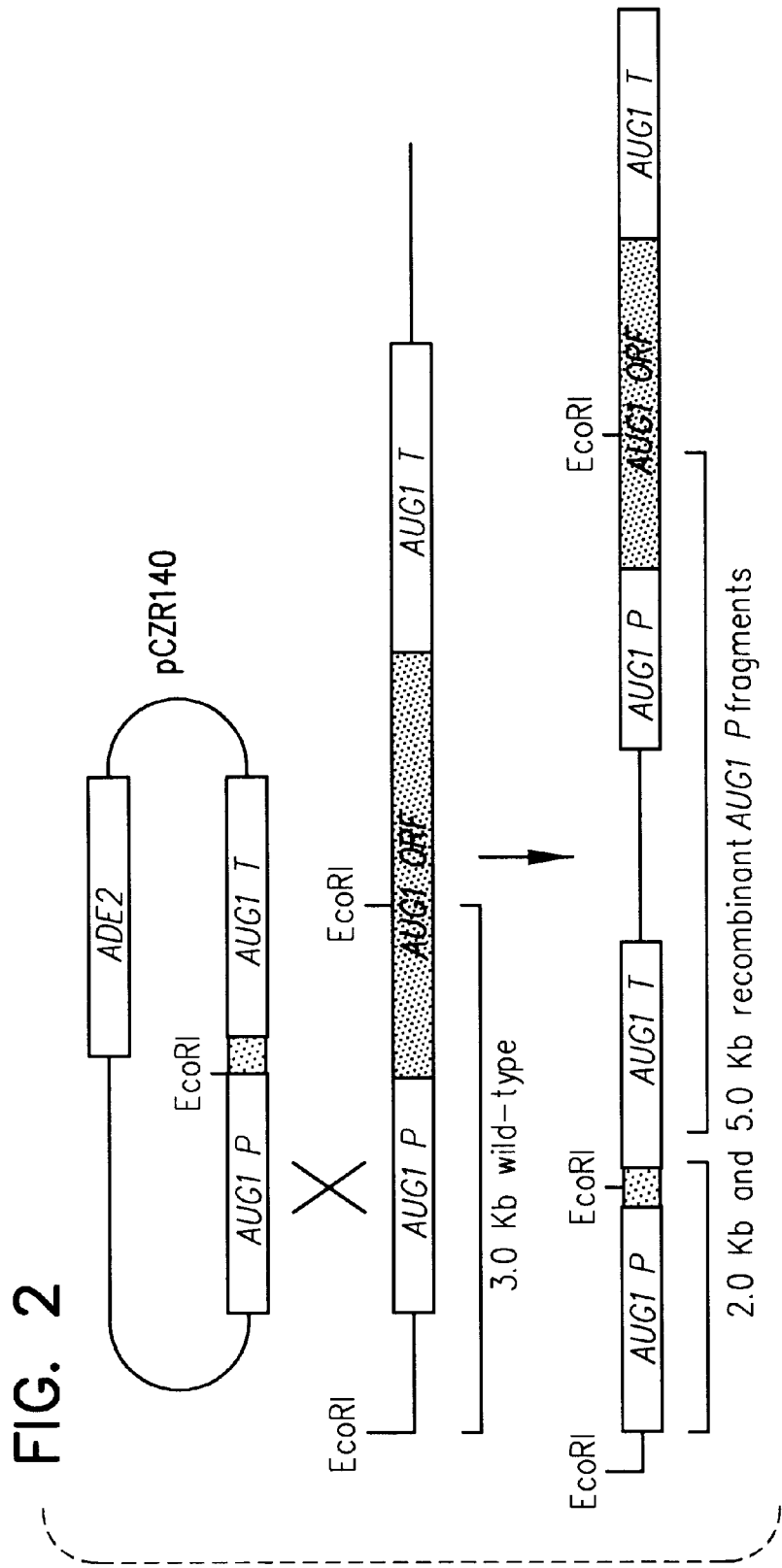
FIG. 2 is a schematic diagram of a recombination event between plasmid pCZR140 and *P. methanolica* genomic DNA.

*P. methanolica* ade2 strain #11 was transformed to Ade+ with Asp I-digested pCZR140, a Bluescript® (Stratagene Cloning Systems, La Jolla, Calif.)-based vector containing the *P. methanolica* ADE2 gene and a mutant of AUG1 in which the entire open reading frame between the promoter and terminator regions has been deleted (FIG. 2). Genomic DNA was prepared from wild-type and transformant cells grown for two days on YEPD plates at 30° C. About 100–200 ml of cells was suspended in 1 ml $H_2O$, then centrifuged in a microcentrifuge for 30 seconds. The cell pellet was recovered and resuspended in 400 μl of SCE+ DTT+zymolyase (1.2 M sorbitol, 10 mM Na citrate, 10 mM EDTA, 10 mM DTT, 1–2 mg/ml zymolyase 100T) and incubated at 37° C. for 10–15 minutes. 400 μl of 1% SDS was added, and the solution was mixed until clear. 300 μl of 5 M potassium acetate, pH 8.9 was added, and the solution was mixed and centrifuged at top speed in a microcentrifuge for five minutes. 750 μl of the supernatant was transferred to a new tube and extracted with an equal volume of phenol/ chloroform. 600 ml of the resulting supernatant was recovered, and DNA was precipitated by the addition of 2 volumes of ethanol and centrifugation for 15 minutes in the cold. The DNA pellet was resuspended in 50 μl TE (10 mM Tris pH 8, 1 mM EDTA)+100 μg/ml RNAase for about 1 hour at 65° C. 10 μl DNA samples were digested with Eco RI (5 μl) in a 100 μl reaction volume at 37° C. overnight. DNA was precipitated with ethanol, recovered by centrifugation, and resuspended in 7.5 μl TE+2.5 μl 5× loading dye. The entire 10 μl volume was applied to one lane of a 0.7% agarose in 0.5×TBE (10×TBE is 108 g/L Tris base 7–9, 55 g/L boric acid, 8.3 g/L disodium EDTA) gel. The gel was run at 100 V in 0.5×TBE containing ethidium bromide. The gel was photographed, and DNA was electrophoretically transferred to a positively derivatized nylon membrane (Nytran® N+, Schleicher & Schuell, Keene, N.H.) at 400 mA, 20 mV for 30 minutes. The membrane was then rinsed in 2×SSC, blotted onto denaturation solution for five minutes, neutralized in 2×SSC, then cross-linked damp in a UV crosslinker (Stratalinker®, Stratagene Cloning Systems) on automatic setting. The blot was hybridized to a PCR-generated AUG1 promoter probe using a commercially available kit (ECL™ kit, Amersham Corp., Arlington Heights, Ill.). Results indicated that the transforming DNA altered the structure of the AUG1 promoter DNA, consistent with a homologous integration event (FIG. 2).

Figure 3:
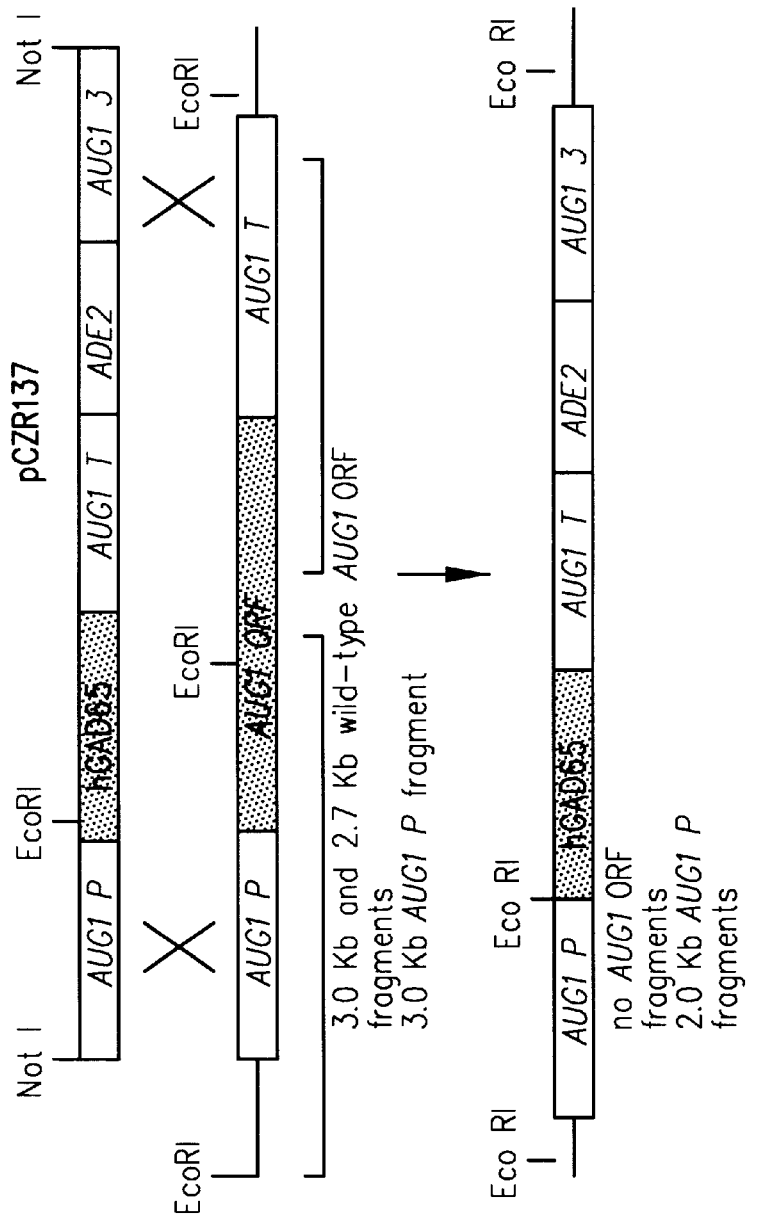
FIG. 3 is a schematic diagram of a recombination event between plasmid pCZR137 and *P. methanolica* genomic DNA.

In a second experiment, P. methanolica ade 2 strain #11 was transformed to Ade+ with Not I-digested pCZR137, a vector containing a human GAD65 cDNA between the AUG1 promoter and terminator (FIG. 3). Genomic DNA was prepared as described above from wild-type cells and a stable, white, Ade+ transformant and digested with Eco RI. The digested DNA was separated by electrophoresis and blotted to a membrane. The blot was probed with a PCR-generated probe corresponding to either the AUG1 open reading frame or the AUG1 promoter. Results demonstrated that the AUG1 open reading frame DNA was absent from the transformant strain, and that the AUG1 promoter region had undergone a significant rearrangement. These results are consistent with a double recombination event (transplacement) between the transforming DNA and the host genome (FIG. 3).

F. An AUG1 strain of P. methanolica is grown in high-density fermentation conditions. The fermentation vessel is charged with mineral salts by the addition of 57.8 g (NH$_4$)$_2$SO$_4$, 46.6 g KCl, 30.8 g MgSO$_4$.7H$_2$O, 8.6 g CaSO$_4$.2H$_2$O, 2.0 g NaCl, and 10 ml antifoam (PPG). H$_2$O is added to bring the volume to 2.5 L, and the solution is autoclaved 40 minutes. After cooling, 350 ml of 50% glucose, 250 ml 10×trace elements (Table 5), 210 ml of 30% NaPhosphate, 25 ml 200 μg/ml biotin, and 250 ml cell inoculum are added. Cells are batch-fed glucose or glucose/methanol in three phases. In phase 1, the cells receive 0.4%/L/hour glucose (w/v final fermentation volume) for 25 hours using 750 g glucose, 110 g (NH$_4$)$_2$SO$_4$, and 278 ml 10×trace elements per 1.5 liter. The cells are then given a transition feed of 0.2% glucose, 0.2% methanol/L/hour for 5 hours. The final glucose-supplemented methanol feed contains 0.1% glucose, 0.4% methanol/L/hr for 25 hours. Final biomass is about 300 g/L cell paste.

G. For fermentation of a P. methanolica aug1Δ strain, the fermentation vessel is initially charged with mineral salts, glucose, phosphate, trace elements and biotin as disclosed in Section F, above. 250 ml of cell inoculum is added. A glucose feed is prepared using 600 g glucose, 108 g (NH$_4$)$_2$SO$_4$, and 273 ml 10×trace elements per 1.2 liter. The cells are batch-fed in three phases. In the first phase, the cells receive glucose for 12 to 25 hours at 0.4%/L/hour. The cells are then induced with a bolus addition of 1% methanol by weight and transitioned to methanol utilization with a mixed 0.2% glucose/0.1% methanol feed for 10 hours. In the third phase, a mixed feed of 0.2% glucose, 0.2% methanol is delivered for 15 hours.

H. P. methanolica cells in which the AUG1 gene had been disrupted by insertion of a GAD65 expression construct retained the ability to grow on methanol, indicating that a second alcohol oxidase gene was present. The second gene, designated AUG2, was identified by PCR. Sequence analysis of the 5' coding region of the gene showed that the N-terminus of the encoded protein was similar to those of known alcohol oxidase genes.

Strain MC GAD8, a transformant that grew very poorly on minimal methanol broth, was used as a source for cloning the AUG2 gene. Genomic DNA was prepared from MC GAD8 and amplified with sense and antisense PCR primers specific for the AUG1 open reading frame (8784, SEQ ID NO:5; 8787, SEQ ID NO:6). A product identical in size to the AUG1 product but showing very low intensity on an analytical gel was obtained.

The putative AUG2 PCR product was digested with a battery of restriction enzymes. Partial digestion by Eco RI and Pvu I, and the presence of several Bgl II sites suggested that the DNA was contaminated with small amounts of AUG1. To remove the contaminating AUG1 DNA, the PCR mixture was cut with Eco RI and gel purified. Since the MC GAD 8 product did not appear to have an Eco RI site, it was unaffected. The resulting gel-purified DNA was reamplified and again analyzed by restriction digestion. The DNA gave a different restriction map from that of the AUG1 PCR product.

Southern blot analysis was performed on genomic DNA from MC GAD8 and wild-type cells using either AUG1 or AUG2 open reading frame PCR fragments as probes. The AUG2 probe hybridized at low stringency to the AUG1 locus and at both low and high stringency to a second locus. The AUG1 probe bound to both loci at low stringency, but bound predominantly to the AUG1 locus at high stringency. These data indicated that the new PCR product from MC GAD8 was similar to but distinct from AUG1. Sequence analysis showed an 83% identity between AUG1 and AUG2 gene products.

To clone the AUG2 genomic locus, PCR primers were designed from the original AUG2 PCR fragment. Primers 9885 (SEQ ID NO:7) and 9883 (SEQ ID NO:8) were used to screen a P. methanolica genomic library. A positive clone bank pool was then probed with the original MC GAD8 PCR product. Cells were plated on 10 plates at about 5000 colonies/plate and grown overnight, then the plates were overlayed with filter discs (Hybond-N, Amersham Corp., Arlington Heights, Ill.). Colonies were denatured, neutralized, and UV cross-linked. Bacterial debris was washed from the filters with 5×SSC, and the filters were again cross-linked. Blots were pre-hybridized in pairs at 42° C. for 1 hour in 25 ml hybridization buffer. Approximately 250 ng of probe was then added to each pair of filters. Hybridization was conducted at 42° C. for four hours. The blots were then washed in 500 ml of 0.1×SSC, 6M urea, 0.4% SDS at 42° C. for 10 minutes, four times. The blots were then neutralized with 500 ml of 2×SSC at room temperature for 5 minutes, two rinses. The blots were then immersed in 100 ml development reagent (ECL, Amersham Corp.).

Positive colonies were picked and amplified using PCR primers 9885 (SEQ ID NO:7) and 9883 (SEQ ID NO:8) to confirm their identity. Positive pools were streaked on plates, and single colonies were rescreened by PCR. One colony was selected for further analysis (restriction mapping and sequencing). A partial sequence of the AUG2 gene is shown in SEQ ID NO:9. As shown in SEQ ID NO:9, the AUG2 sequence begins at the HindIII site a nucleotide 91. Nucleotides upstream from this position are vector sequence. The coding sequence begins at nucleotide 170.

Disruption of the AUG2 gene had little effect on cell growth on methanol. Cells lacking both functional AUG1 and AUG2 gene products did not grow on methanol. Subsequent analysis showed that the AUG1 gene product is the only detectable alcohol oxidase in cells grown in a fermentor.

EXAMPLE 4

Purification of GAD65 from *P. methanolica*

To extract GAD65 from the *P. methanolica* yeast expressing GAD65 as described in Example 3, the yeast are milled in a DYNO-MILL while keeping chilled at or below 5° C. The extraction buffer contains protease inhibitors as well as the detergent Triton X-114. The buffer components are: 40 mM HEPES, 10 mM DTT, 10 mM EDTA, 200 µM pyridoxal phosphate (PL), 1 mM aminoethyl-isothiouroniumbromide hydrobromide (AET), 2% (v/v) Triton X-114, 25 µg/ml aprotinin, 5 µg/ml leupeptin, 5 µg/ml soybean trypsin inhibitor, 5 µg/ml pepstatin A, and 0.1 mM PMSF. The buffer was adjusted to pH 7.2. This same buffer, with 0.2% Triton X-114, containing the above protease inhibitors, is the primary buffer used in the subsequent chromatography steps. It will be referred to in this Example as primary GAD buffer (PGB).

For extract clarification and GAD65 capture (to be performed in a cold room), the extract from the DYNO-MILL has a measured pH of 6.1 and is titrated to pH of 7.2 before centrifugation. The extract is centrifuged 0.5 hours at 3,500 rpm in a 1 liter swinging bucket Beckman centrifuge at 5° C. to pellet a significant portion of cell debris. The pellet is re-suspended in extraction buffer and re-extracted for a minimal period of time (~10 min.) at which point it is again spun in the centrifuge. The supernants are combined, chilled on slurry ice overnight, again centrifuged as described above, and a small but noticeable white precipitate is removed. The supernatant is adjusted to pH 8.5 with 2N NaOH and diluted (~3.5x) in PGB (in this case pH 8.5) until the conductivity is 3 to 4 mmho. This material is loaded at 50 ml/min. over an 11 cm diameter, 1 liter bed of Whatman DE-52 anion exchanger equilibrated in the pH 8.5 PGB, at the final TX-114 concentration of 1% (v/v) at 3 to 4 mmho conductivity. The 1% TX-114 facilitates solubilization/stability of the bound and subsequently eluted GAD. Upon completing the sample load, the column is washed for 10 column volumes with equilibration buffer, after which the bound protein is "step" eluted with to equilibration buffer containing 0.4 M NaCl at 22.4 mmho conductivity and adjusted to lo TX-114 with 3x "pre-condensed" Triton X-114. The bulk of the GAD65 activity detectable by Western blotting is recovered within 4 column volumes of collected eluate. This pool is now ready for the phase partitioning step in the purification process described below.

For phase partitioning, the TX-114 concentration of the eluted pool from above (only 1% (v/v) TX-114) is adjusted to 2% (v/v) TX-114 through the addition of an appropriate volume of pre-condensed TX-114 to the pool. The total volume of the adjusted pool is further diluted 1:2 with 2% TX-114 (again precondensed) PGB. This mixture is poured into an 11 cm diameter column with a bottom outlet fitted with a stopcock, and the filled column is moved from the cold room (~4° C.) to a warm room (30° C.) and allowed to partition overnight. A dense lower layer forms, and a visible interface between the Triton-rich lower phase and the detergent-depleted upper phase is observable. The stopcock is opened, and the condensed Triton, GAD65-containing, phase is harvested. An initial large fraction is gathered, and when it becomes apparent that the phase boundary is about to pass through the column outlet smaller fractions are taken until a noticeable increase in the afflux flow rate is observed (signifying the arrival of the less viscous depleted phase at the condenser outflow). The harvested condensed phase contains significantly purified GAD65 as determined by Coomassie SDS-PAGE analysis.

The harvested GAD65 Triton phases are diluted in PGB, pH=8.0, until the conductivity is less than or equal to 4 mmho. The material is then applied to bed of Q-Sepharose Fast Flow anion exchanger (Pharmacia), equilibrated in PBG at pH 8.0 and modified by replacing the HEPES with a combination of 20 mM Tris, 20 mM MES, 20 mM Mops, and 20 mM acetate to allow the generation of a smooth pH gradient. This buffer also contains 0.1% octylglucoside instead of TX-114. Upon completing the sample load, the column is washed with 10 column volumes of equilibration buffer. A 22 column volume gradient is formed between the pH 8.0 equilibration buffer and the same buffer at pH 4.9. A linear pH gradient from pH 8.0 to 4.9 is formed, with the GAD65 eluting from pH 7.4 down to 5.0. Later eluting fractions contain a greater degree of contamination, yet the purity of the GAD65 increases markedly. Before the elution is begun, the test tubes in the fraction collector are augmented with enough AET and Tris base to adjust the final sample volume to 10 mM in AET and bring the sample to pH 7.2±0.2. The tubes are quickly mixed upon sample collection to ensure the mixing of the collected sample with the AET and Tris base.

For hydroxyapatite chromatography, the GAD65 containing fractions from the above pH gradient-eluted Q-Sepharose column are pooled. The pH of the pool is adjusted, if necessary, to between 6.8 to 7.0. The conductivity of this pool is 7.0 mmho. This material is applied to a bed of ceramic hydroxyapatite previously equilibrated in the multibuffer system used in the Q-Sepharose step, but at pH 6.8 to 7.0 and containing 10 mM AET to facilitate the elution of concentrated GAD65 and improve the solubility of the eluted protein.

Coomassie-stained SDS-PAGE gels of samples purified as disclosed above show large bands, up to 20 µg of GAD65 per lane, with an estimated purity of 90? or better.

Thus, the present invention provides high level expression of GAD65, up to 500 mg/L or more, in methylotrophic yeast. The use of methylotrophic yeast make production of GAD65 feasible on an industrial scale by virtue of the ease of fermentation and the precisely controlled induction of GAD65 expression. When purified from the methylotrophic yeast, especially according to the purification protocols described herein, the recombinant GAD65 has high specific activity and retains antigenic characteristics of the native molecule that are essential to using GAD65 in immunological assays and therapeutic protocols.

Although the foregoing invention has been described in some detail by way of illustration and example for purposes of clarity of understanding, it will be obvious that certain changes and modifications may be practiced within the scope of the appended claims.

What is claimed is:

1. A methylotrophic yeast which grows on methanol as a carbon and energy source, transformed with a DNA construct comprising the following operatively linked elements:
    a) a methanol-inducible transcriptional promoter;
    b) a DNA segment encoding a GAD65 polypeptide;
    c) a transcriptional terminator; and
    d) a selectable marker,
which yeast when cultured in a fermentor expresses said GAD65 polypeptide at a concentration of at least 500 mg/L.

2. The methylotrophic yeast of claim 1, wherein the methylotrophic yeast is Pichia, Hansenula or Candida.

3. The methylotrophic yeast of claim 1, wherein the methanol-inducible promoter of the transforming DNA construct is from the same species as the methylotrophic yeast transformed with the DNA construct.

4. The methylotrophic yeast of claim 1, wherein the transcriptional terminator of the DNA construct is from an alcohol oxidase gene.

5. The methylotrophic yeast of claim 1, wherein the GAD65 polypeptide is human GAD65.

6. The methylotrophic yeast of claim 1, wherein the methylotrophic yeast is *Pichia methanolica*.

7. The methylotrophic yeast of claim 2, wherein the methylotrophic yeast is *Pichia pastoris* or *Pichia methanolica*.

8. The methylotrophic yeast of claim 2, wherein the methanol-inducible promoter of the transforming DNA construct is from an alcohol oxidase gene.

9. The methylotrophic yeast of claim 6, wherein the transcriptional terminator of the DNA construct is from a *P. pastoris* AOX1 gene.

10. The methylotrophic yeast of claim 8, wherein the alcohol oxidase gene is *P. pastoris* AOX1.

11. The methylotrophic yeast of claim 8, wherein the methylotrophic yeast: is *Pichia pastoris*.

12. A method for producing a GAD65 polypeptide comprising the steps of:
    culturing a methylotrophic yeast which grows on methanol as a carbon and energy source, transformed with a DNA construct which comprises the following operatively linked elements:

a) a methanol-inducible transcriptional promoter;
b) a DNA segment encoding a GAD65 islet cell polypeptide;
c) a transcriptional terminator; and
d) a selectable marker, in a culture medium,, whereby said GAD65 polypeptide is produced at a concentration of at least 500 mg/L in said culture medium.

13. The method of claim 12, wherein the methanol-inducible promoter is from an alcohol oxidase gene.

14. The method of claim 12, wherein the DNA segment encoding a GAD65 islet cell polypeptide encodes human GAD65.

15. The method of claim 13, wherein the alcohol oxidase gene is *P. pastoris* AOX1.

16. The method of claim 13, wherein the transcriptional terminator is from an alcohol oxidase gene.

17. The method of claim 16, wherein the alcohol oxidase gene is *P. pastoris* AOX1.

18. A method for purifying GAD65 expressed by a culture of methylotrophic yeast cells, which comprises the steps of:
   isolating a GAD65-containing cell fraction from the yeast cell culture in a buffer containing a reducing agent and a detergent;
   phase-partitioning the GAD65-containing cell fraction into a GAD65-containing detergent phase and an aqueous phase;
   separating the GAD65 from the GAD65-containing detergent phase by a first anion exchange chromatography in a buffer containing a reducing agent and a detergent to produce a first GAD65 anion exchange fraction;
   applying the first GAD65 anion exchange fraction to a column containing a cation exchange medium at a slightly acidic pH and adjusting the GAD65-containing fraction therefrom to an alkaline pH;
   loading the GAD65 cation exchange fraction on a second anion exchange column at an alkaline pH in a buffer containing a reducing agent and a detergent, eluting the GAD65 in an alkaline to acid pH gradient, and adjusting the pH of the GAD65 eluate to about neutral; and
   purifying the GAD65 anion exchange eluate by hydroxyapatite chromatography in a buffer containing a reducing agent and a detergent, and obtaining purified GAD65.

19. The method of claim 18, wherein the GAD65containing cell fraction is isolated from the yeast cell culture by lysing the yeast cells.

20. The method of claim 18, further comprising the step of, prior to separating the GAD65 from the GAD65-containing detergent phase by the first anion exchange chromatography, removing yeast cell particulate from the GAD65-containing detergent phase.

21. The method of claim 18, wherein the cation exchange medium is a sulfopropyl cation exchange medium.

22. The method of claim 18, wherein the second anion exchange column is a quaternary ammonium anion exchange column.

23. The method of claim 18, wherein the GAD65 eluting pH gradient is developed between pH 8 and pH 4.

24. The method of claim 18, wherein the GAD65 is eluted from the hydroxyapatite with a gradient of potassium phosphate.

25. The method of claim 18, wherein the methylotrophic yeast cells are a species of Pichia or Hansenula.

26. The method of claim 18, wherein the GAD65 is human GAD65.

27. The method of claim 18, wherein the reducing agent is dithiothreitol or 2-mercaptoethanol.

28. The method of claim 18, wherein the detergent is a non-ionic detergent.

29. The method of claim 18, wherein the methylotrophic yeast cells are *Pichia pastoris* or *Pichia methanolica*.

30. The method of claim 28, wherein the non-ionic detergent is polyethylene glycol tertiary octylphenyl ether, polyethylene glycol mono (p-(1,1,3,3-tetramethyl-butyl) phenyl) ether, or n-octylglucoside.

31. A. A method for purifying GAD65 expressed by a culture of methylotrophic yeast cells, which comprises the steps of:
   isolating a GAD65-containing cell fraction from the yeast cell culture in a buffer containing a reducing agent and a detergent;
   applying the GAD65-containing cell fraction to a first anion exchange column in a buffer containing a reducing agent and a detergent to produce a first GAD65 anion exchange fraction;
   phase-partitioning the first GAD65 anion exchange fraction into a GAD65-containing detergent phase and an aqueous phase;
   loading the GAD65-containing detergent phase on a second anion exchange column at an alkaline pH in a buffer containing a reducing agent and a detergent, eluting the GAD65 in an alkaline to acid pH gradient, and adjusting the pH of the GAD65 eluate to about neutral; and
   purifying the GAD65 anion exchange eluate by hydroxyapatite chromatography in a buffer containing a reducing agent and a detergent, and obtaining purified GAD65.

32. The method of claim 31, wherein the GAD65containing cell fraction is isolated from the yeast cell culture by lysing the yeast cells.

33. The method of claim 31, further comprising the step of, prior to applying the GAD65-containing cell fraction to the first anion exchange column, removing yeast cell particulate from the GAD65-containing cell fraction.

34. The method of claim 31, wherein the second anion exchange column is a quaternary ammonium anion exchange column.

35. The method of claim 31, further comprising fractionating the first GAD65 anion exchange fraction on hydroxyapatite before phase-partitioning.

36. The method of claim 31, wherein the GAD65 eluting pH gradient is developed between pH 8 and pH 4.

37. The method of claim 31, wherein the GAD65 is eluted from the hydroxyapatite with a gradient of potassium phosphate.

38. The method of claim 31, wherein the methylotrophic yeast cells are a species of Pichia or Hansenula.

39. The method of claim 31, wherein the GAD65 is human GAD65.

40. The method of claim 38, wherein the methylotrophic yeast cells are *Pichia pastoris* or *Pichia methanolica*.

41. A method of preparing a methylotrophic yeast strain that produces a GAD65 polypeptide comprising the steps of:
   a) transforming a methylotrophic yeast host with a DNA construct which comprises the operatively linked elements of (i) a methanol-inducible transcriptional promoter, (ii) a DNA segment encoding a GAD65 polypeptide, (iii) a transcriptional terminator, and (iv) a selectable marker;
   b) culturing the transformed cells from step (a) under conditions wherein the DNA segment is expressed and GAD65 polypeptide is produced;
   c) assaying the level of GAD65 polypeptide produced by isolates of the transformed cells; and d) selectively culturing isolates that produce levels of GAD65 polypeptide of at least 500 mg/L.

42. A *Pichia methanolica* yeast strain transformed with a DNA construct comprising the following operatively linked elements:

a) a methanol-inducible transcriptional promoter;

b) a DNA segment encoding a GAD65 polypeptide;

c) a transcriptional terminator; and d) a selectable marker.

43. The *Pichia methanolica* yeast strain of claim 42, wherein the methanol-inducible promoter of the transforming DNA construct is from an alcohol oxidase gene.

44. The *Pichia methanolica* yeast strain of claim 42, wherein the transcriptional terminator of the DNA construct is from an alcohol oxidase gene.

45. The *Pichia methanolica* yeast strain of claim 42, wherein the transcriptional terminator of the DNA construct is from a *P. pastoris* AOX1 gene.

46. The *Pichia methanolica* yeast strain of claim 42, wherein the GAD65 polypeptide is human GAD65.

47. The *Pichia methanolica* yeast strain of claim 42, which when cultured in a fermentor expresses said GAD65 polypeptide at a concentration of at least 50 mg/L.

48. The *Pichia methanolica* yeast strain of claim 43, wherein the alcohol oxidase gene is *P. pastoris* AOX1.

49. The *Pichia methanolica* yeast strain of claim 47, which when cultured in a fermentor expresses said GAD65 polypeptide at a concentration of up to 500 mg/L or greater.

50. A method for producing a GAD65 polypeptide comprising the steps of:

culturing a *Pichia methanolica* yeast strain transformed with a DNA construct which comprises the following operatively linked elements:

a) a methanol-inducible transcriptional promoter;

b) a DNA segment encoding a GAD65 islet cell polypeptide;

c) a transcriptional terminator; and d) a selectable marker in a culture medium,, whereby said GAD65 polypeptide is produced in said culture medium.

51. The method of claim 50, wherein the methanol-inducible promoter is from an alcohol oxidase gene.

52. The method of claim 50, wherein the transcriptional terminator is from an alcohol oxidase gene.

53. The method of claim 50, wherein the DNA segment encoding a GAD65 islet cell polypeptide encodes human GAD65.

54. The method of claim 50, wherein said methylotrophic yeast transformed with said DNA construct expresses said GAD65 polypeptide at a concentration greater than 500 mg/L.

55. The method of claim 51, wherein the alcohol oxidase gene is *P. pastoris* AOX1.

56. The method of claim 52, wherein the alcohol oxidase gene is *P. pastoris* AOX1.

* * * * *